(12) United States Patent
Ahmed et al.

(10) Patent No.: US 10,151,681 B2
(45) Date of Patent: Dec. 11, 2018

(54) OPTOFLUIDIC FLOW METER

(71) Applicant: The United States of America, as represented by the Secretary of Commerce, Washington, DC (US)

(72) Inventors: Zeeshan Ahmed, Gaithersburg, MD (US); Gregory A. Cooksey, Gaithersburg, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/673,299

(22) Filed: Aug. 9, 2017

(65) Prior Publication Data

US 2018/0275041 A1    Sep. 27, 2018

Related U.S. Application Data

(60) Provisional application No. 62/477,383, filed on Mar. 27, 2017.

(51) Int. Cl.
*G01N 15/14* (2006.01)
*G01F 1/38* (2006.01)
(Continued)

(52) U.S. Cl.
CPC .... *G01N 15/1404* (2013.01); *B01L 3/502761* (2013.01); *G01F 1/386* (2013.01);
(Continued)

(58) Field of Classification Search
CPC .. G01F 15/006; G01F 15/185; G01N 15/4404
See application file for complete search history.

(56) References Cited

U.S. PATENT DOCUMENTS 5,178,153 A * 1/1993 Einzig ................. A61B 5/0261
356/477
6,740,866 B1    5/2004 Bohnert et al.
(Continued)

FOREIGN PATENT DOCUMENTS

EP    1008840 A1    6/2000
WO    2011013111 A2    2/2011

OTHER PUBLICATIONS

Holmes, C., et al., Integrated optical differential pressure transducers achieved using thin buckled silica membranes and direct UV written planar Bragg gratings, Sensors and Actuators, Mar. 21, 2011, 14-21, 168.

(Continued)

*Primary Examiner* — Jewel V Dowtin
(74) *Attorney, Agent, or Firm* — Office of Chief Counsel for National Institute of Standards and Technology

(57) ABSTRACT

An optofluidic flow meter to determine a rate of fluid flow in a flow member includes: the flow member; a primary fluid conduit disposed in the flow member and that receives a fluid; a secondary fluid conduit disposed in the flow member; and a fiber optic comprising a fiber Bragg grating interposed between a first flow region of the primary fluid conduit and a second flow region of the secondary fluid conduit and that: physically distorts relative to a pressure differential between the primary fluid conduit and the secondary fluid conduit; and produces a shift in a Bragg wavelength in response to a physical distortion due to the pressure differential.

14 Claims, 28 Drawing Sheets

(51) Int. Cl.
*G01F 15/18* (2006.01)
*G01F 15/00* (2006.01)
*G02B 6/02* (2006.01)
*B01L 3/00* (2006.01)

(52) U.S. Cl.
CPC .......... *G01F 15/006* (2013.01); *G01F 15/185* (2013.01); *G02B 6/02076* (2013.01)

(56) References Cited

U.S. PATENT DOCUMENTS

| | | | |
|---|---|---|---|
| 6,910,388 B2 * | 6/2005 | Jones | G01F 1/44 73/861.63 |
| 7,254,008 B2 | 8/2007 | Xie et al. | |
| 7,894,061 B2 * | 2/2011 | MacDougall | G01F 1/7086 250/227.18 |
| 8,528,383 B2 | 9/2013 | Evans et al. | |
| 9,162,226 B2 | 10/2015 | Cooksey et al. | |
| 2004/0168523 A1 * | 9/2004 | Fernald | G01F 1/666 73/861.01 |
| 2015/0204743 A1 | 7/2015 | Nieuwland | |

OTHER PUBLICATIONS

Holmes, C., "Direct UV Written Planar Devices for Sensing and Telecommunication Applications", University of Southhampton, PhD Thesis, 2009.

Gau, C., et al., Piezoresistive characteristics of MWNT nanocomposites and fabrication as a polymer pressure sensor, Nanotechnology, 2009, 185503, 20.

Jin, Y., et al., Measuring the pressures across microfluidic droplets with an optical tweezer, Optics Express, 2012, 24450-24464, vol. 20 No. 22.

Muller, M., et al., Shear strain influence on fiber bragg grating measurement system, Journal of Lightwave Technology, 2009, 5223-5229, vol. 27 No. 23.

Orth, A., et al., Elastomer membrane pressure sensors for microfluidics, International Conference on Miniaturized Systems for Chemistry and Life Sciences, 2010, 1994-1996.

Poeggel, S., et al., Optical fibre pressure sensors in medical applications, Sensors, 2015, 17115-17148, 15.

Sekimori, Y., et al., Pressure sensor for micro chemical system on a chip, IEEE, 2004, 516-519.

Sheng, H-J., et al. A lateral pressure sensor using a fiber bragg grating, IEEE Photonics Technology Letters, 2004, 1146-1148, vol. 16 No. 4.

Song, W., et al., Optofluidic membrane interferometer: An imaging method for measuring microfluidic pressue and flow rate simultaneously on a chip, Biomicrofluidics, 2011, 044110, 5.

Srivastava, N., et al., Microfluidic pressure sensing using trapped air compression, Lab Chip, 2007, 633-637, 7.

Wu, C-Y., et al., Integrated ionic liquid-based electrofluidic circuits for pressure sensing within polydimethylsiloxane microfluidic systems, Lab on a Chip, 2011, 1740-1746, 11.

* cited by examiner (A)

(B)

OPTOFLUIDIC FLOW METER

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an optofluidic flow meter to determine a rate of fluid flow in a flow member, the optofluidic flow meter comprising: the flow member; a primary fluid conduit disposed in the flow member and that receives a fluid; a secondary fluid conduit disposed in the flow member; and a fiber optic comprising a fiber Bragg grating interposed between a first flow region of the primary fluid conduit and a second flow region of the secondary fluid conduit and that: physically distorts relative to a pressure differential between the primary fluid conduit and the secondary fluid conduit; and produces a shift in a Bragg wavelength in response to a physical distortion due to the pressure differential.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
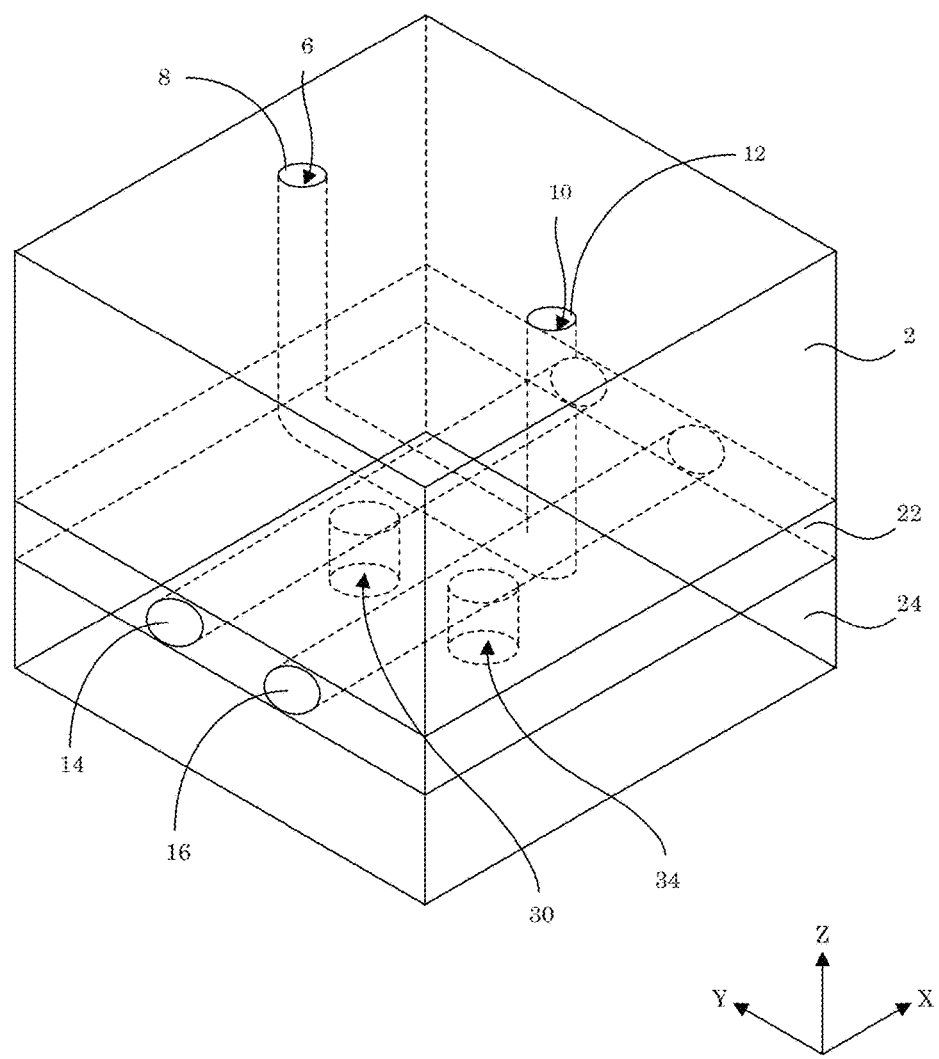
FIG. 1 shows an optofluidic flow meter.
Figure 2:
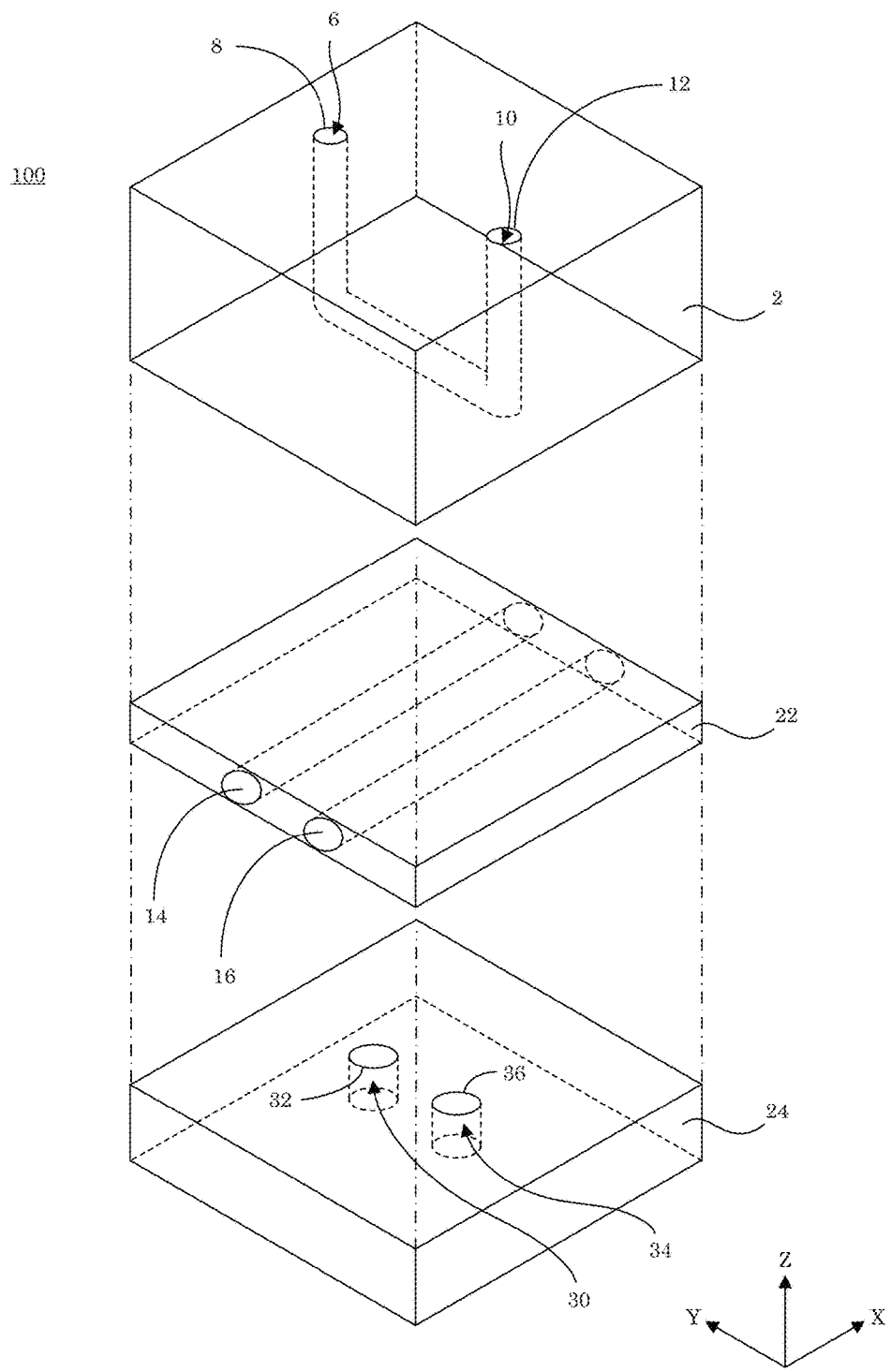
FIG. 2 shows an exploded view of the optofluidic flow meter shown in FIG. 1.
Figure 3:
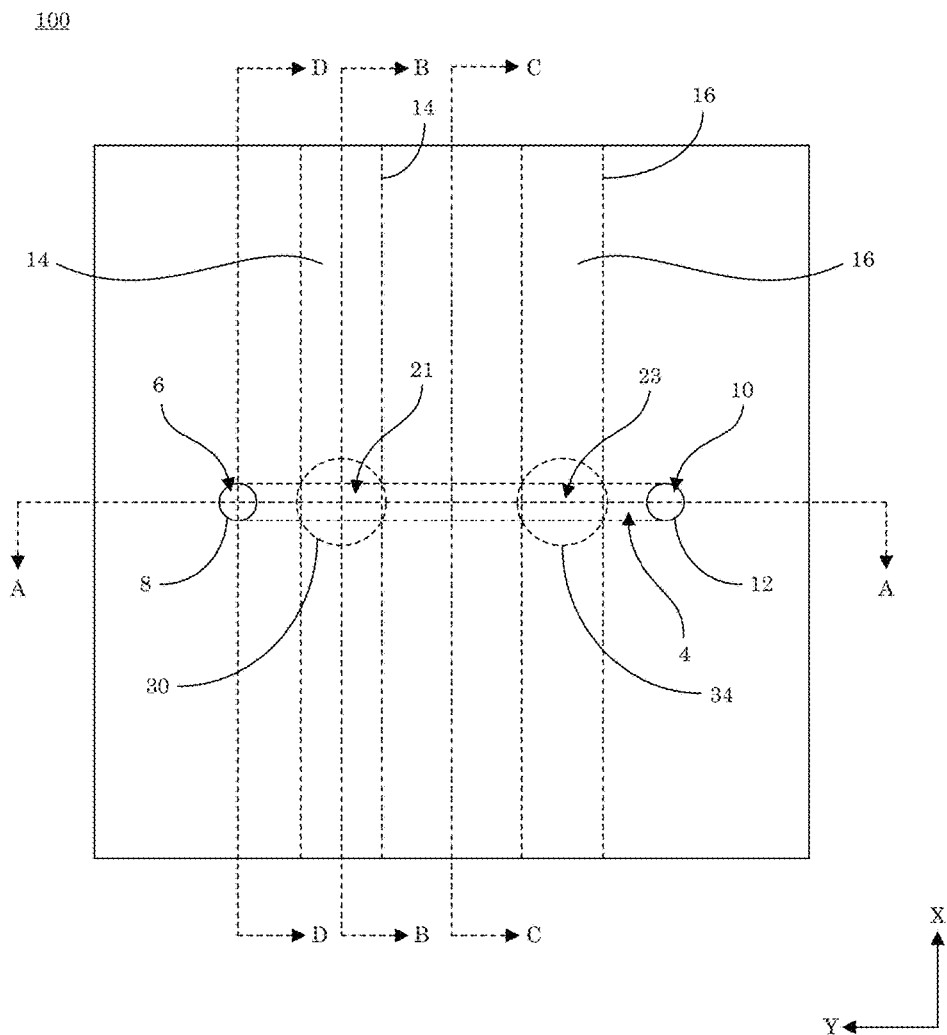
FIG. 3 shows a top view of the optofluidic flow meter shown in FIG. 1.
Figure 4:
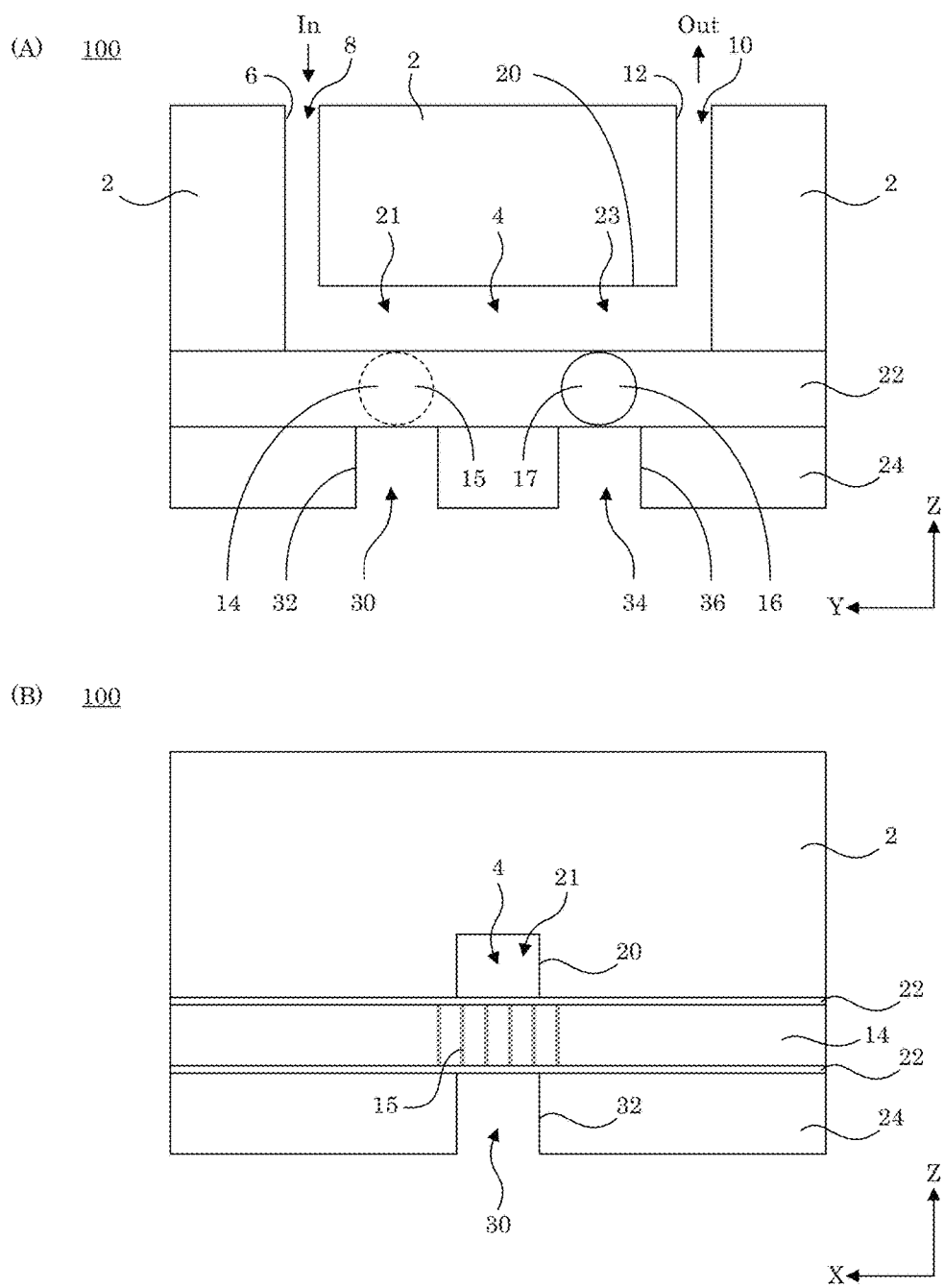
FIG. 4 shows a cross-section along line A-A of the optofluidic flow meter shown in FIG. 3 in panel A, and panel B shows a cross-section along line B-B.
Figure 5:
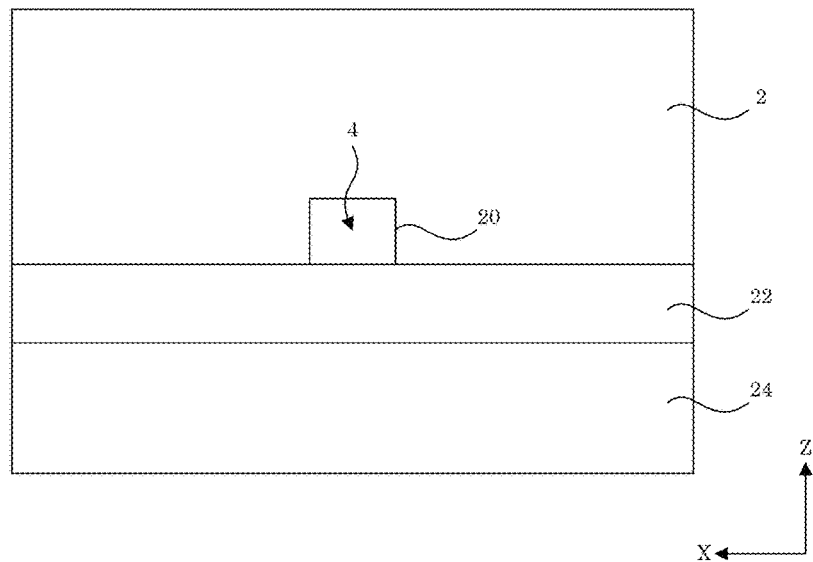
FIG. 5 shows a cross-section along line C-C of the optofluidic flow meter shown in FIG. 3 in panel A, and panel B shows a cross-section along line D-D.
Figure 5:
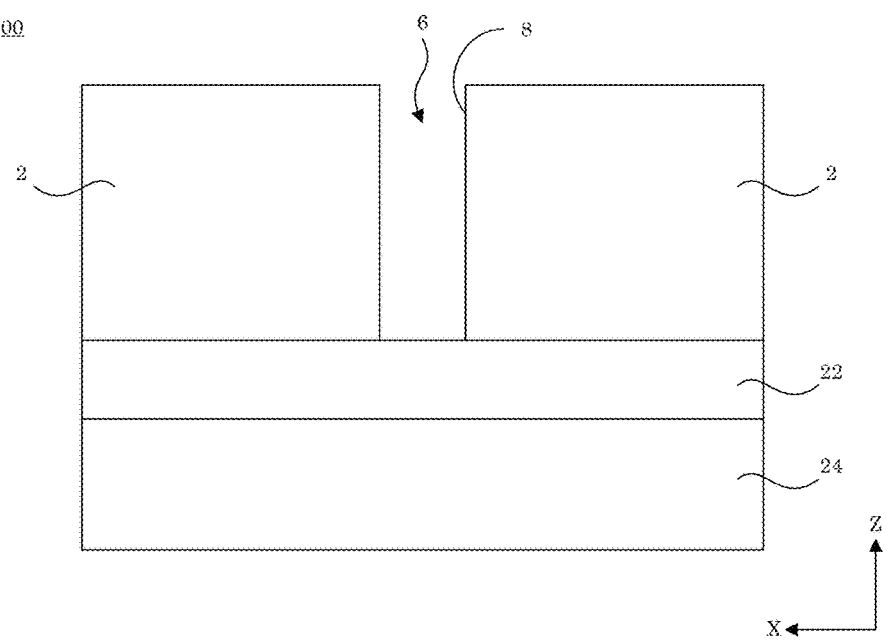
Figure 6:
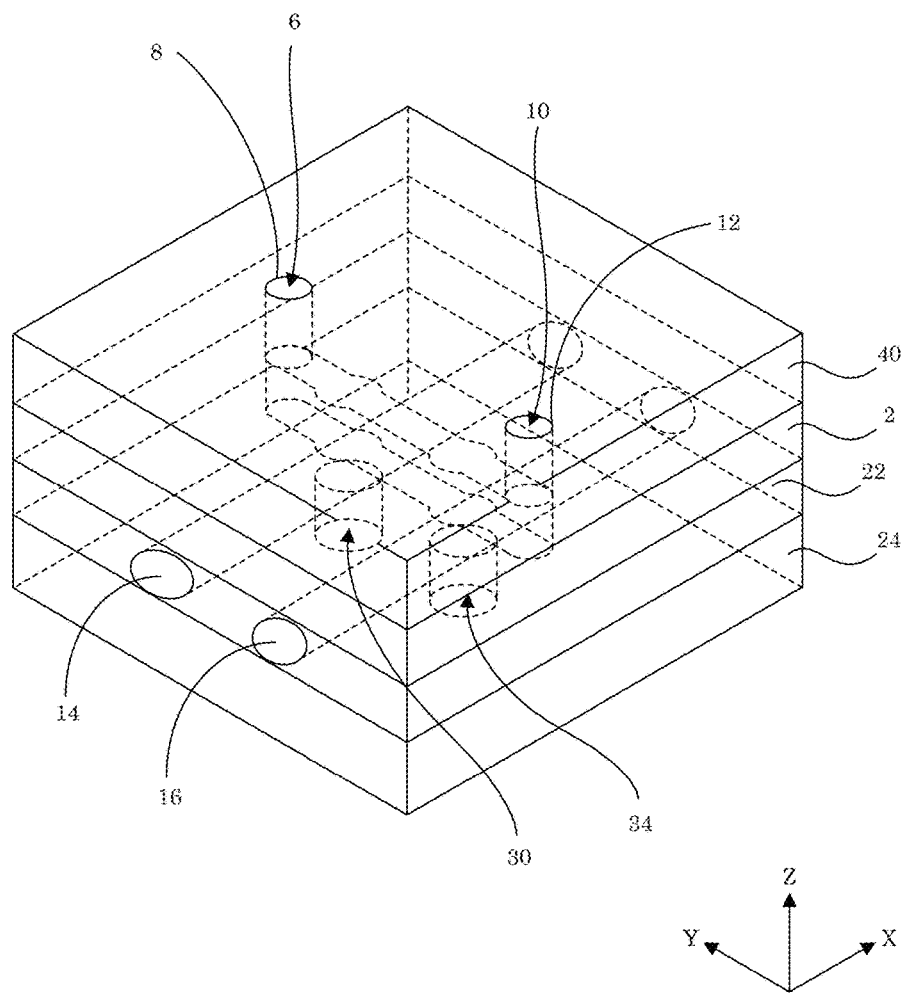
FIG. 6 shows an optofluidic flow meter.
Figure 7:
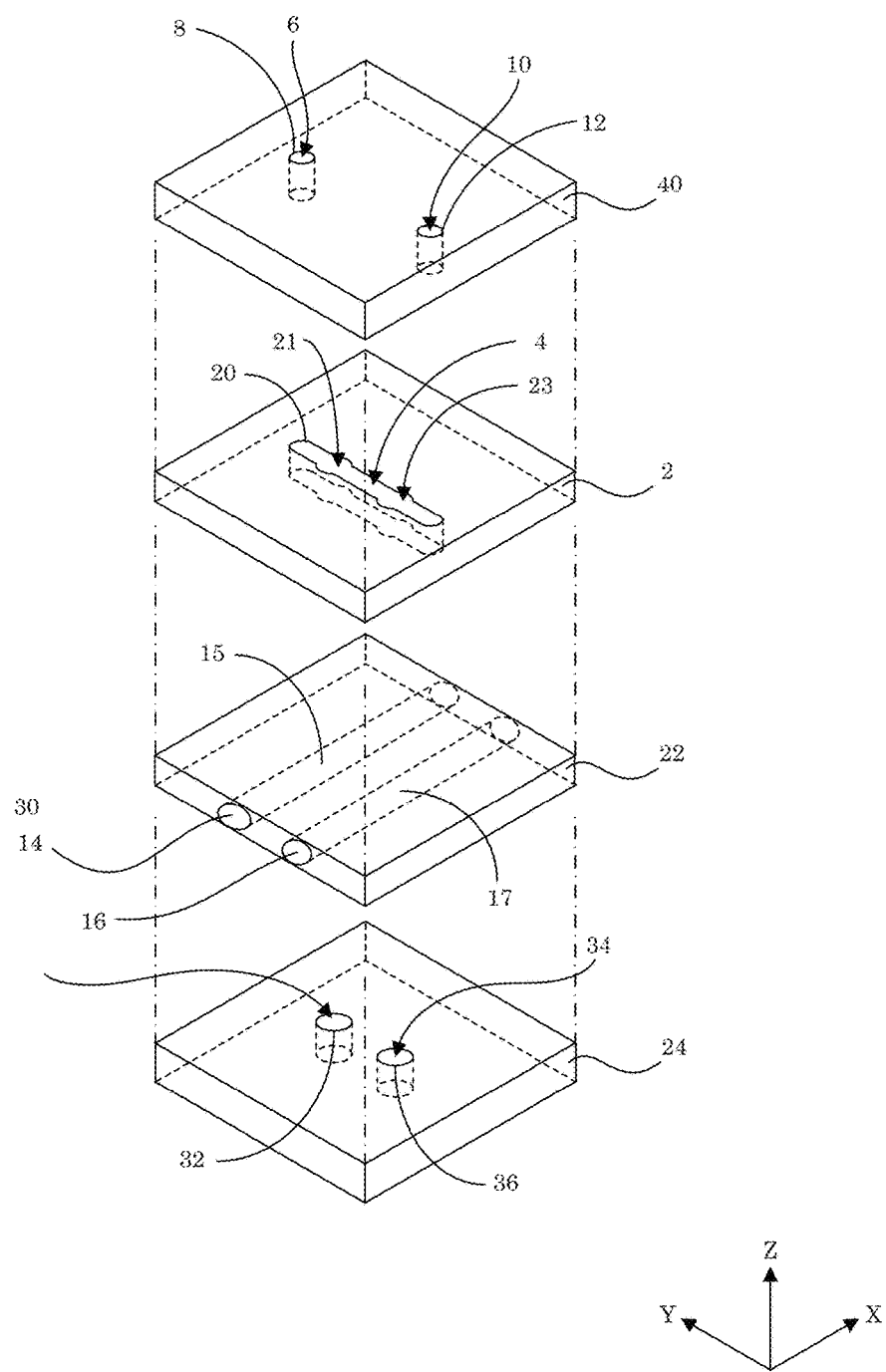
FIG. 7 shows an exploded view of the optofluidic flow meter shown in FIG. 6.
Figure 8:
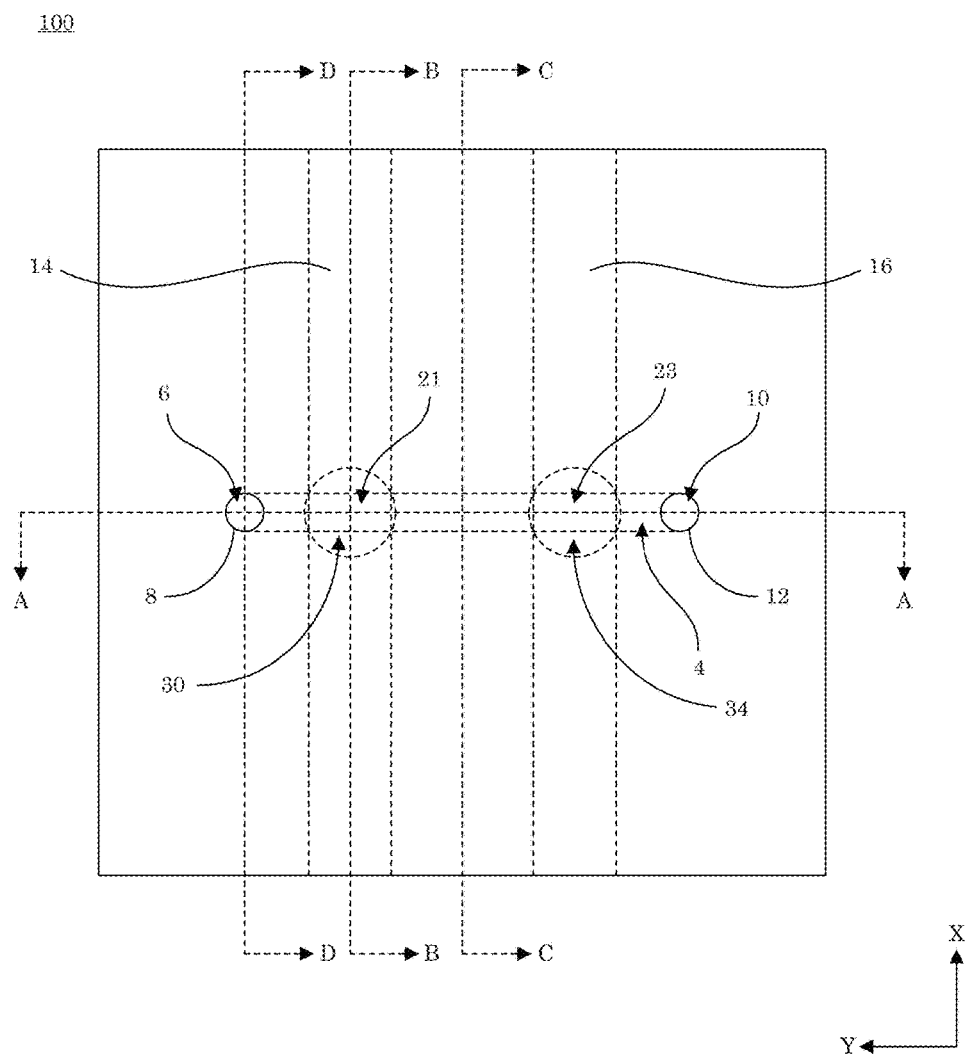
FIG. 8 shows a top view of the optofluidic flow meter shown in FIG. 6.
Figure 9:
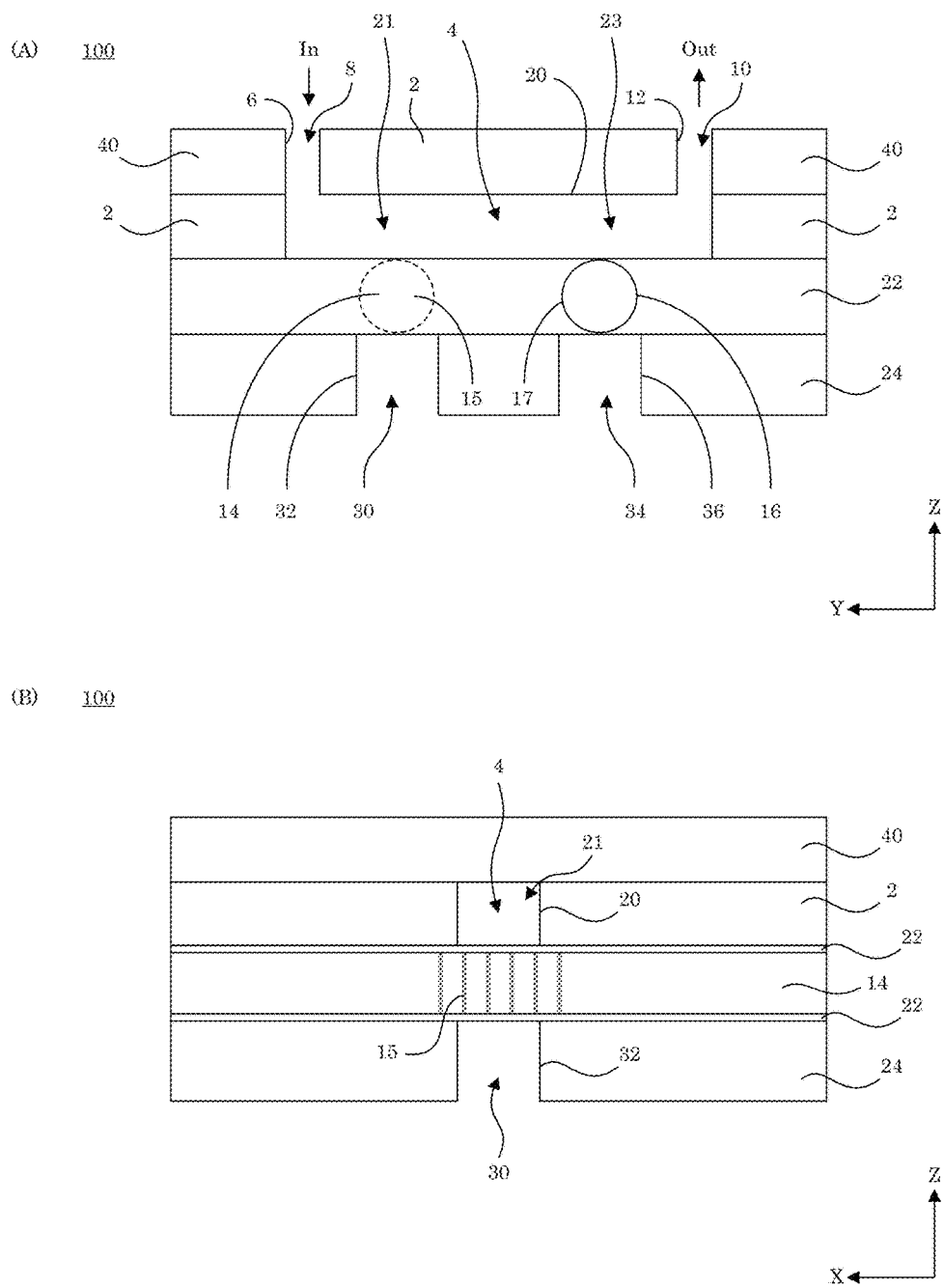
FIG. 9 shows a cross-section along line A-A of the optofluidic flow meter shown in FIG. 8 in panel A, and panel B shows a cross-section along line B-B.
Figure 10:
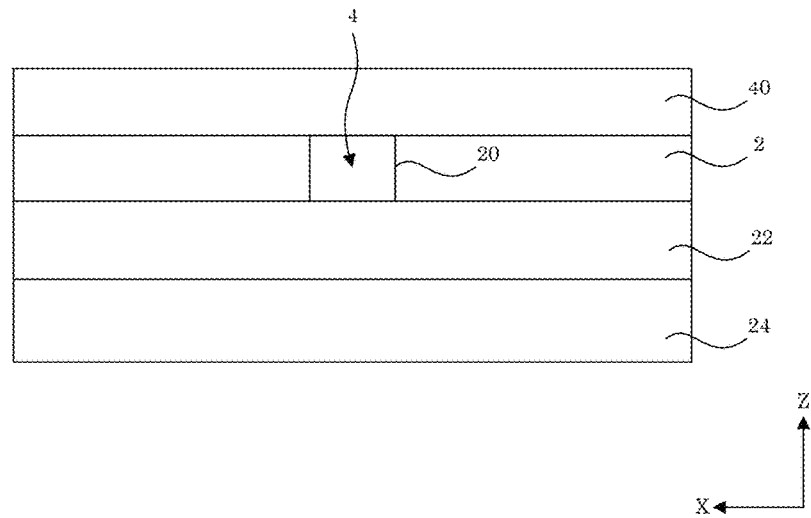
FIG. 10 shows a cross-section along line C-C of the optofluidic flow meter shown in FIG. 8 in panel A, and panel B shows a cross-section along line D-D.
Figure 10:
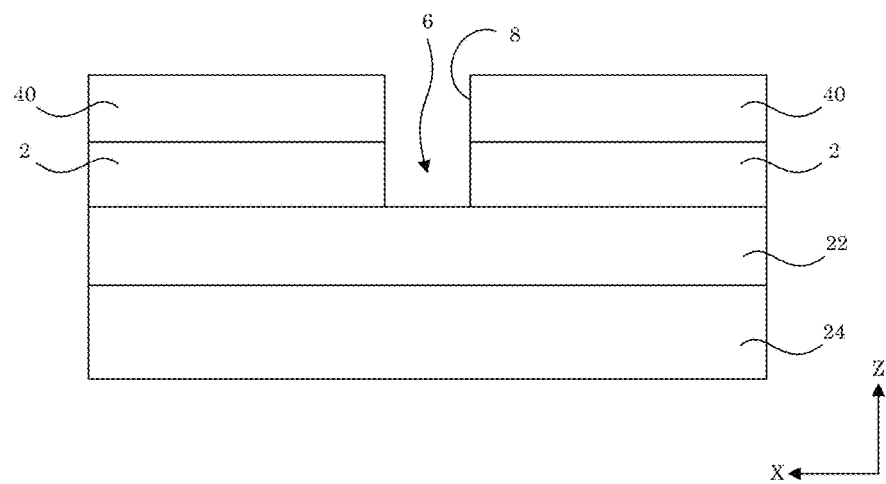
Figure 11:
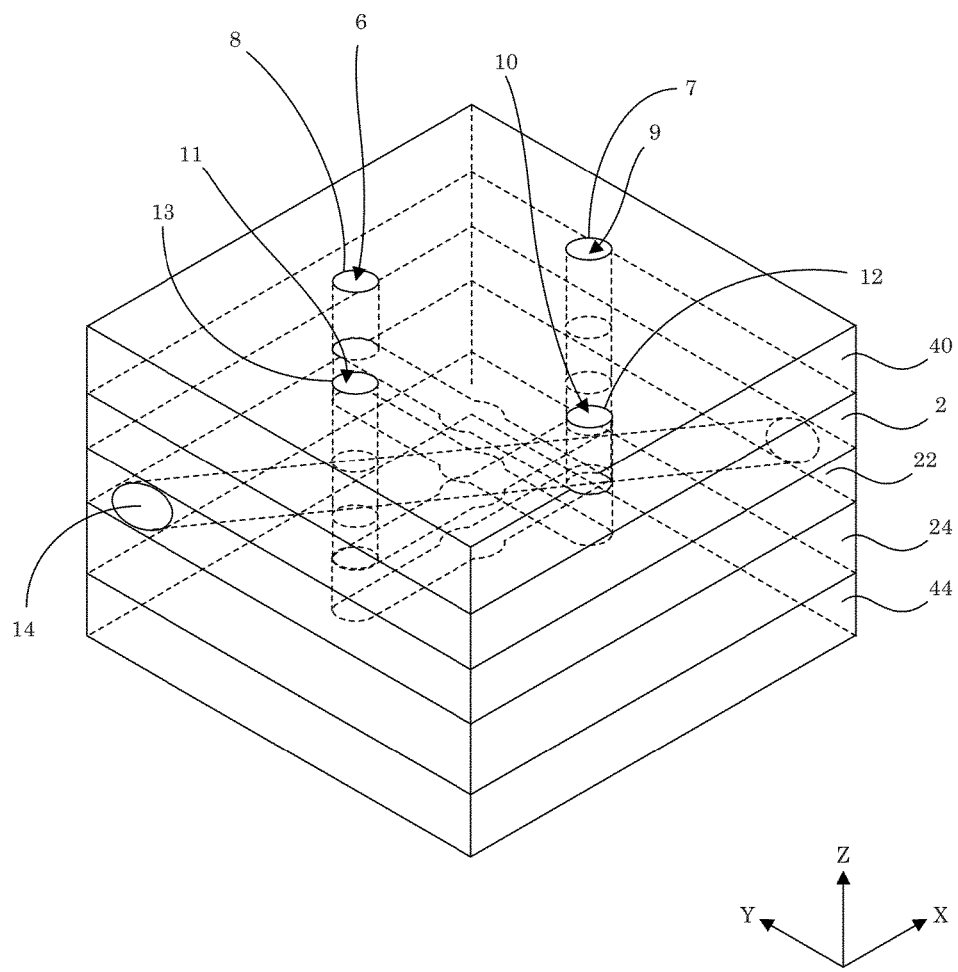
FIG. 11 shows an optofluidic flow meter.
Figure 12:
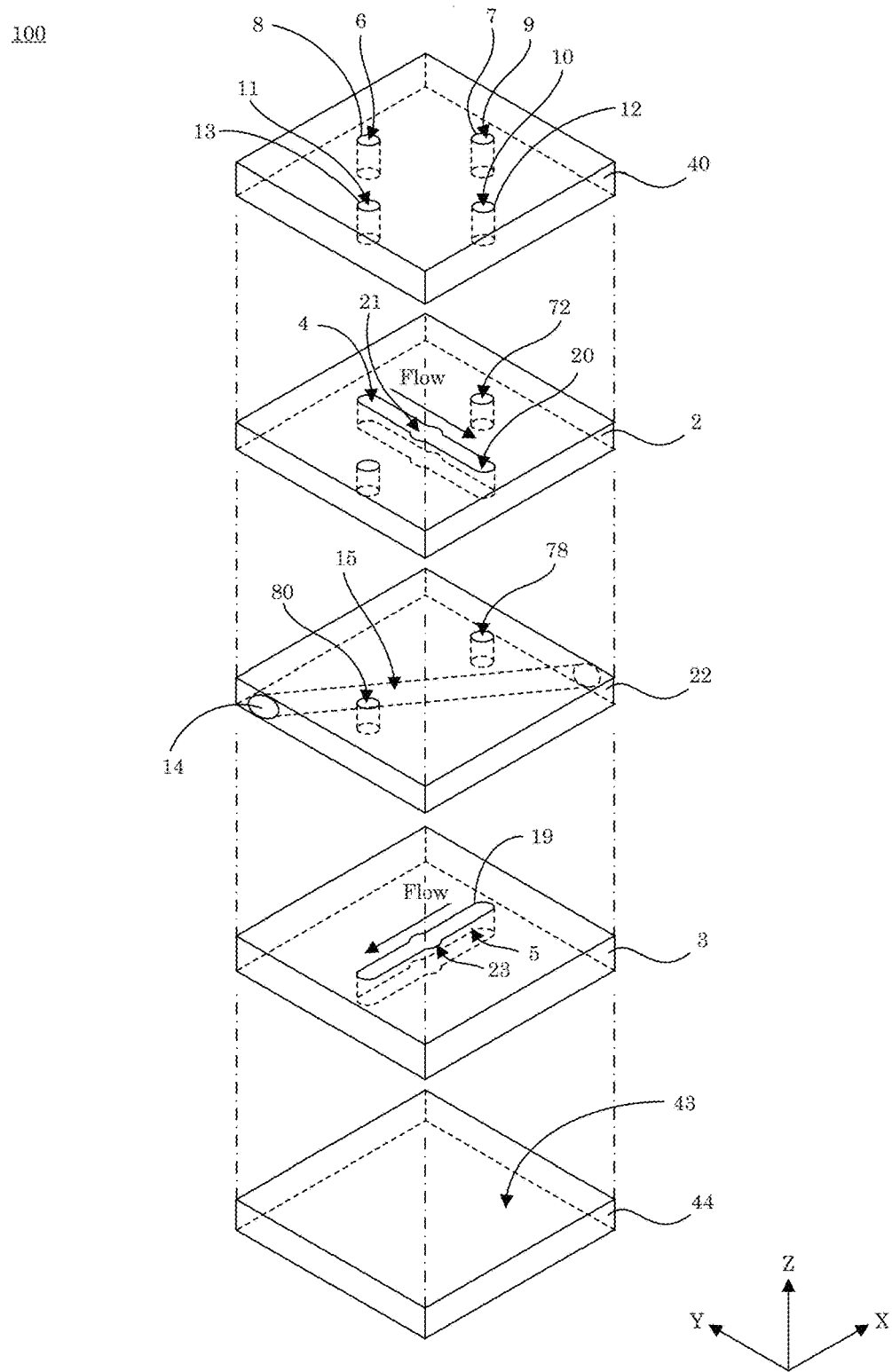
FIG. 12 shows an exploded view of the optofluidic flow meter shown in FIG. 11.
Figure 13:
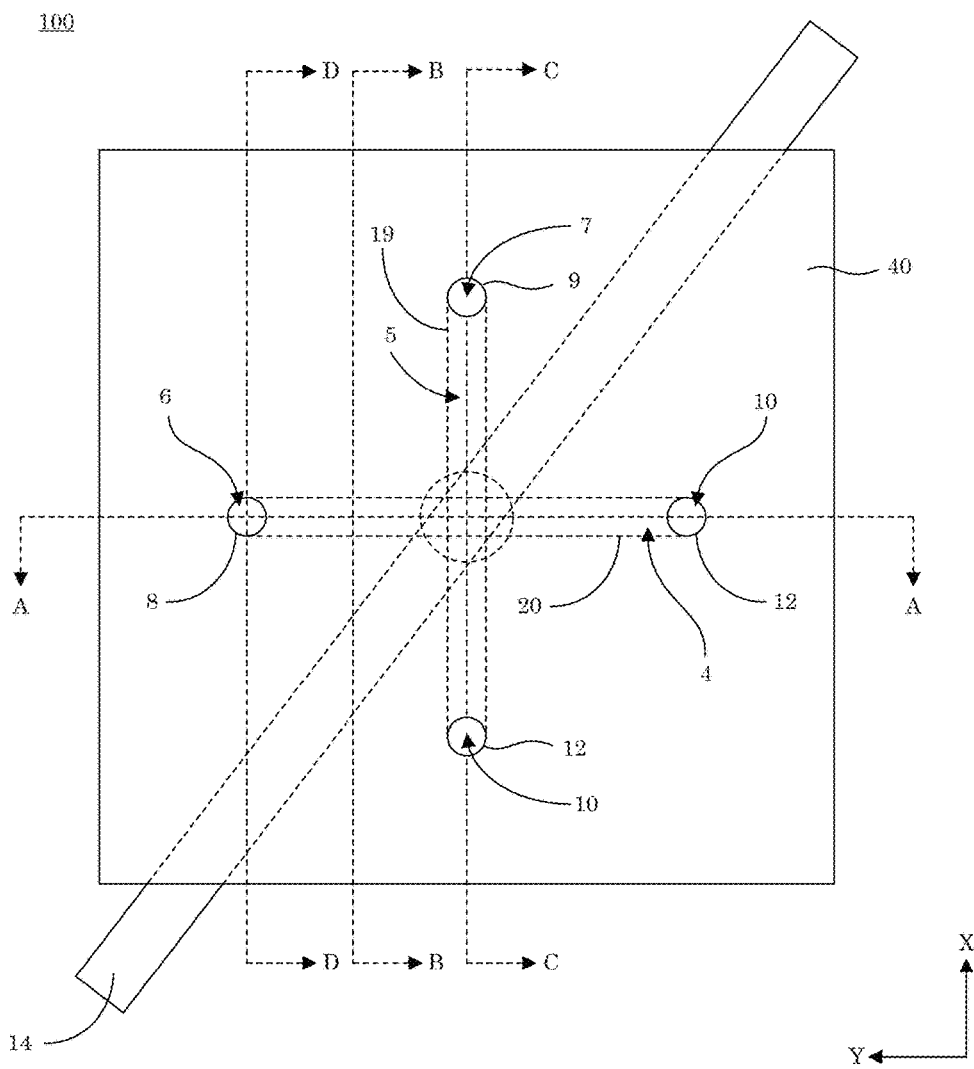
FIG. 13 shows a top of the optofluidic flow meter shown in FIG. 11.
Figure 14:
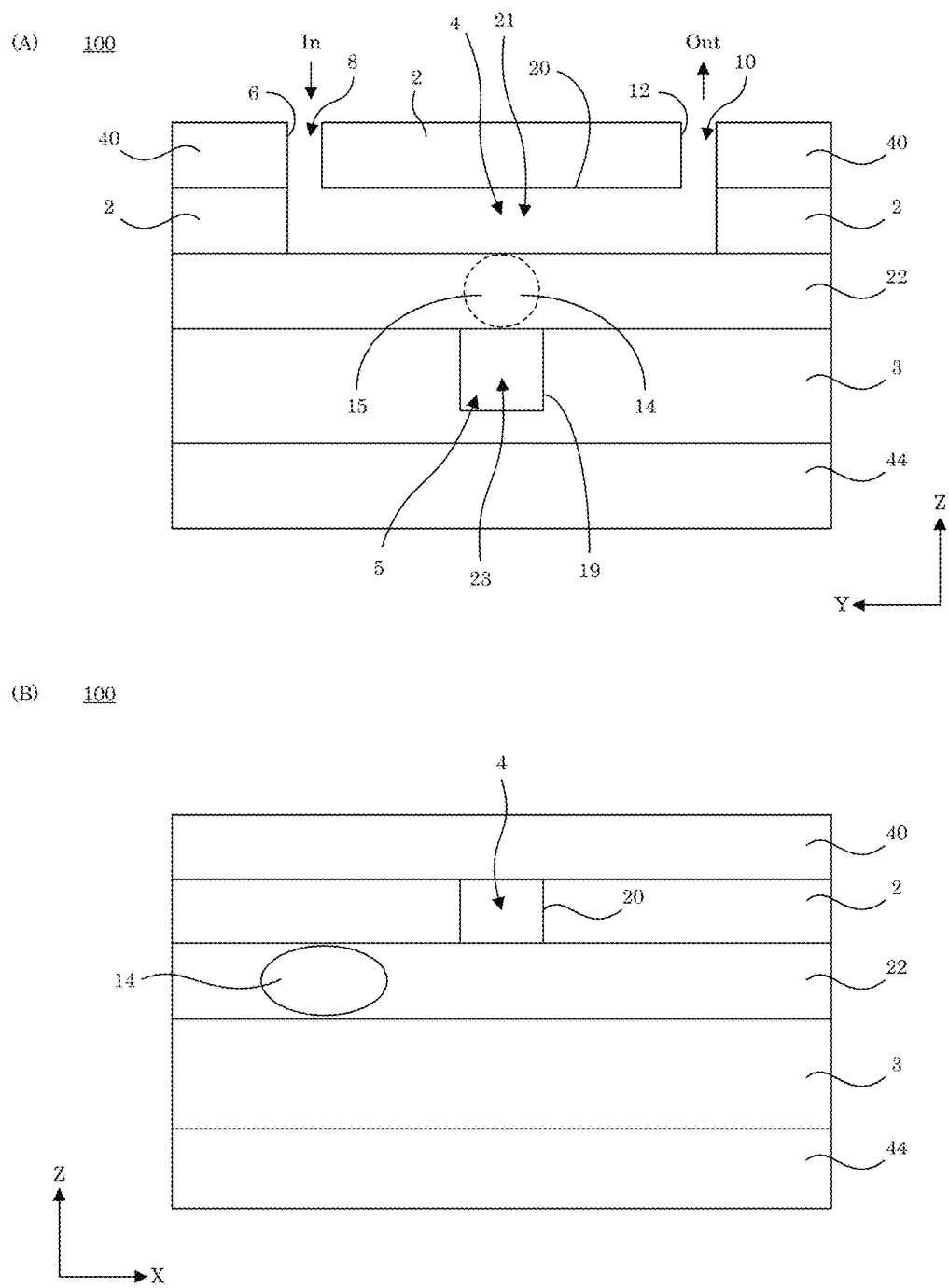
FIG. 14 shows a cross-section along line A-A of the optofluidic flow meter shown in FIG. 13 in panel A, and panel B shows a cross-section along line B-B.
Figure 15:
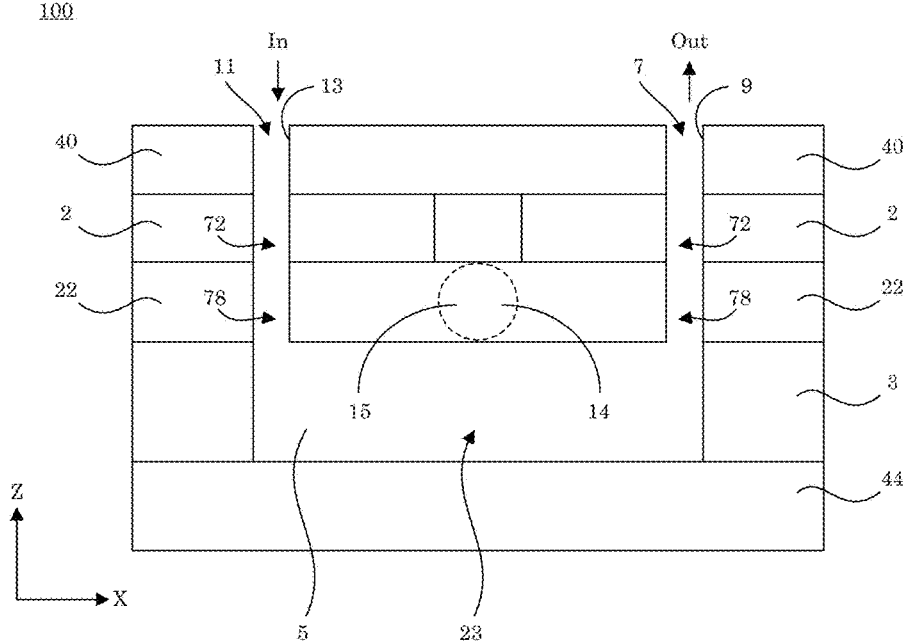
FIG. 15 shows a cross-section along line C-C of the optofluidic flow meter shown in FIG. 13 in panel A, and panel B shows a cross-section along line D-D.
Figure 15:
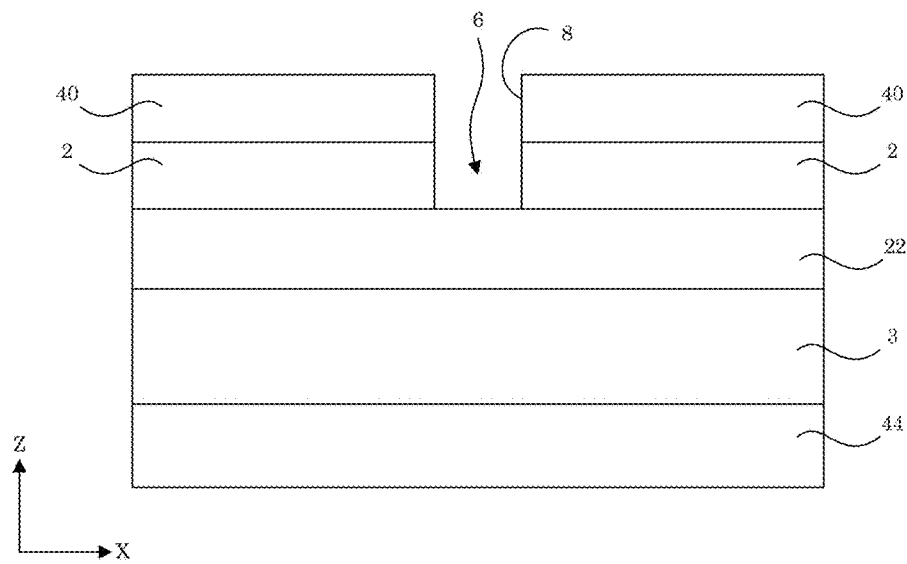

A detailed description of one or more embodiments is presented herein by way of exemplification and not limitation.

It has been discovered that an optofluidic flow meter herein provides sensing strain on the optofluidic flow meter produced in response to a force, pressure, or the like subjected to the optofluidic flow meter by a fluid flowing in a fluid conduit. Unexpectedly and advantageously, the optofluidic flow meter provides measurement of microscale forces (pressures) for a fluid carrying article. In an embodiment, the optofluidic flow meter includes an optical fiber and includes a fiber Bragg grating (FBG), which is an optical fiber having a refractive index grating that reflects a selected wavelength of light, i.e., a Bragg wavelength. The Bragg wavelength changes, i.e., shifts to a shorter wavelength or longer wavelength, in response to a mechanical strain (or temperature change) of the optical fiber. In some embodiments, the FBG is attached to or embedded within a flexible support, e.g., a flexible membrane, that is disposed proximate to the fluid conduit. In this matter, the optofluidic flow meter provides a determination of pressure relative to pressure of the atmosphere around the optofluidic flow meter. In a certain embodiment, the FBG of the optofluidic flow meter is interposed between the plurality of fluid conduit (e.g., two fluid conduits), wherein the FBG is sensitive to a differential pressure between the fluid conduits. Here, fluid in a fluid conduit physically distorts, e.g., deflects, the flexible membrane and strains the fiber optic according to pressure.

It is contemplated that fluid flowing from one surface of the flexible membrane to an opposing surface of the flexible membrane physically distorts the flexible membrane according to the differential pressure, e.g., a pressure drop, between flow regions where the fluid crosses the membrane in which the FBG is disposed. In combination with a fluidic resistance that can depend upon a dimension or predetermined fluidic resistance of the fluid conduit, the pressure drop provided by the shift in the Bragg wavelength by the optofluidic flow meter provides determination of flow rate.

In an embodiment, with reference to FIG. 1, FIG. 2, FIG. 3, FIG. 4, and FIG. 5, optofluidic flow meter 100 determines a rate of fluid flow in flow member 2. Here, optofluidic flow meter 100 includes flow member 2; fluid conduit 4 bounded by wall 20 in combination with flexible member 22 or fiber optic 14 and fiber optic 16 and disposed in flow member 2 and that receives a fluid; first fiber optic 14 including first fiber Bragg grating 15 interposed between first flow region 21 of fluid conduit 4 and receptacle 30 bounded by wall 32 disposed in substrate 24; and second fiber optic 16 including second fiber Bragg grating 17 interposed between second flow region 23 of fluid conduit 4 and receptacle 34 bounded by wall 36 disposed in substrate 24. Optofluidic flowmeter 100 can also include flexible membrane 22, wherein first optical fiber 14 and second optical fiber 16 independently can be disposed on or disposed in flexible membrane 22. Additionally, first fiber optic 14 and second fiber optic 16 physically distort relative to flow member 2 into or away from receptacle 30 or receptacle 34 in response to a change in pressure respectively at first flow region 21 or second flow region 23 of fluid conduit 4. Accordingly, first fiber-optic 14 produces a shift in a first Bragg wavelength of first FBG 15 in response to physical distortion of first fiber optic 14 due to change in pressure at first flow region 21. Moreover, second fiber-optic 16 produces a shift and a second Bragg wavelength of second FBG 17 in response to physical distortion of second fiber optic 16 due to change in pressure that second flow region 23. Further, the fluid disposed in fluid conduit 4 flows through fluid conduit 4 by introduction of the fluid at port 6 bounded by wall 8 disposed in flow member 2. The fluid exits fluid conduit 4 through port 10 bounded by wall 12 disposed in flow member 2. It is contemplated that optofluidic flow meter 100 can be a macroiluidic article through which macro volumes of the fluid flow (e.g., milliliters of fluid per minute (mL/min) or greater) or a microfluidic article through which micro volumes of the fluid flow (e.g., microliters of fluid per minute (A/minute) or less). In an embodiment, optofluidic flow meter 100 is the microfluidic article.

In an embodiment, with reference to FIG. 6, FIG. 7, FIG. 8, FIG. 9, and FIG. 10, optofluidic flow meter 100 includes flow member 2 having fluid conduit 4 that receives fluid; cover 40 disposed on flow member 2 and providing surface 41 that, in combination with wall 20, bounds fluid conduit 4; first fiber optic 14 including first fiber Bragg grating 15 interposed between first flow region 21 of fluid conduit 4 and receptacle 30 bounded by wall 32 disposed in substrate 24; and second fiber optic 16 including second fiber Bragg grating 17 interposed between second flow region 23 of fluid conduit 4 and receptacle 34 bounded by wall 36 disposed in substrate 24. Substrate 24 can be disposed on support 44 that maintains rigidity of substrate 24 relative to physical distortion of first fiber optic 14 and second fiber optic 16. Here, first fiber optic 14 and second fiber-optic 16 physically distort relative to flow member 2 into or away from receptacle 30 or receptacle 34 in response to a change in pressure respectively at first flow region 21 or second flow region 23 of fluid conduit 4. Accordingly, first fiber-optic 14 produces a shift in a first Bragg wavelength of first FBG 15 in response to physical distortion of first fiber optic 14 due to change in pressure at first flow region 21. Moreover, second fiber-optic 16 produces a shift and a second Bragg wavelength of second FBG 17 in response to physical distortion of second fiber-optic 16 due to change in pressure that second flow region 23. Further, the fluid disposed in fluid conduit 4 flows through fluid conduit 4 by introduction of the fluid at port 6 bounded by wall 8 disposed. In cover 40. The fluid exits fluid conduit 4 through port 10 bounded by wall 12 disposed in cover 40.

In an embodiment, with reference to FIG. 11, FIG. 12, FIG. 13, FIG. 14, and FIG. 15, optofluidic flow meter 100 includes flow member 2; primary fluid conduit 4 disposed in first flow member 2 and that receives a first fluid; secondary fluid conduit 5 disposed in second flow member 3 and that receives a second fluid; and fiber optic 14 disposed in flexible membrane 22 and including fiber Bragg grating 15 interposed between first flow region 21 of primary fluid conduit 4 and second flow region 23 of secondary fluid conduit 5 and that: physically distorts relative to a pressure differential between primary fluid conduit 4 and secondary fluid conduit 5, and produces a shift in Bragg wavelength in response to physical distortion of fiber optic 14 due to the pressure differential. Cover 40 is disposed on first flow member 2 and provides surface 41 that, in combination with wall 20, bounds primary fluid conduit 4. Substrate 24 can be disposed on second flow member 3 and provides surface 43 that, in combination with wall 19, bounds secondary fluid conduit 5.

Here, fiber optic 14 physically distorts to protrude into secondary fluid conduit 5 at second flow region 23 of second flow member 3 and away from primary fluid conduit 4 at first flow region 21 when a first pressure P1 of primary fluid conduit 4 is greater than a second pressure P2 of secondary fluid conduit 5, i.e., P1 P2. Also, fiber optic 14 physically distorts to protrude into primary fluid conduit 4 at first flow region 21 of first flow member 2 and away from secondary fluid conduit 5 at second flow region 23 of second flow member 3 when first pressure P1 of primary fluid conduit 4 is less than second pressure P2 of secondary fluid conduit 5, i.e., P1<P2. When first pressure P1 of primary fluid conduit 4 is equal to second pressure P2 of secondary fluid conduit 5, i.e., P1=P2, fiber optic 14 is in a relaxed state instead of being physically distorted. In this manner, fiber optic 14 physically distorts relative to first flow member 2 and second flow member 3 to respond to the pressure differential between primary fluid conduit 4 and secondary fluid conduit 5. Accordingly, fiber optic 14 produces a shift in Bragg wavelength of FBG 15 in response to physical distortion of fiber optic 14 due to change in relative pressure between primary fluid conduit 4 and secondary fluid conduit 5 at first flow region 21 and second flow region 23.

Further, the first fluid disposed in primary fluid conduit 4 is introduced at port 6 bounded by wall 8 disposed in cover 40, flows through primary fluid conduit 4, and exits primary fluid conduit 4 through port 10 bounded by wall 12 disposed in cover 40. Similarly, the second fluid disposed in secondary fluid conduit 5 is introduced at port 7 bounded by wall 9 disposed in cover 40, is communicated through aperture 72 disposed in first flow member 2, is communicated through aperture 78 disposed in flexible membrane 22, flows through secondary fluid conduit 5, is communicated through aperture 80 disposed in flexible membrane 22, is communicated through aperture 74 disposed in first flow member 2, and exits secondary fluid conduit 5 through port 11 bounded by wall 13 disposed in cover 40. It is contemplated that first flow region 21 overlaps second flow region 23 in a presence of FBG 15 fiber optic 14. In this manner, secondary fluid conduit 5 is isolated from fluid communication with primary fluid conduit 4 and receives the second fluid independently from receipt of the first fluid by primary fluid conduit 4.

In an embodiment, with reference to FIG. 16, FIG. 17, FIG. 18, FIG. 19, and FIG. 20, optofluidic flow meter 100 includes first flow member 2; primary fluid conduit 4 disposed in first flow member 2 and that receives a fluid; secondary fluid conduit 5 disposed in second flow member 3 and that receives the fluid from primary fluid conduit 4; and fiber optic 14 disposed in flexible membrane 22 and including fiber Bragg grating 15 interposed between first flow region 21 of primary fluid conduit 4 and second flow region 23 of secondary fluid conduit 5. Fiber optic 14 physically distorts relative to a pressure differential between primary fluid conduit 4 and secondary fluid conduit 5 and also produces a shift in Bragg wavelength in response to physical distortion of fiber optic 14 due to the pressure differential. Cover 40 is disposed on first flow member 2 and provides surface 41 that, in combination with wall 20, bounds primary fluid conduit 4. Substrate 24 can be disposed on second flow member 3 and provides surface 43 that, in combination with wall 19, bounds secondary fluid conduit 5.

Here, fiber optic 14 physically distorts to protrude into secondary fluid conduit 5 at second flow region 23 of second flow member 3 and away from primary fluid conduit 4 at first flow region 21 when a first pressure P1 of primary fluid conduit 4 is greater than a second pressure P2 of secondary fluid conduit 5, i.e., P1>P2. Also, fiber optic 14 physically distorts to protrude into primary fluid conduit 4 at first flow region 21 of first flow member 2 and away from secondary fluid conduit 5 at second flow region 23 of second flow member 3 when first pressure P1 of primary fluid conduit 4 is less than second pressure P2 of secondary fluid conduit 5, i.e., P1<P2. When first pressure P1 of primary fluid conduit 4 is equal to second pressure P2 of secondary fluid conduit 5, i.e., P1=P2, fiber optic 14 is in a relaxed state instead of being physically distorted. In this manner, fiber optic 14 physically distorts relative to first flow member 2 and second flow member 3 to respond to the pressure differential between primary fluid conduit 4 and secondary fluid conduit 5. Accordingly, fiber optic 14 produces the shift in Bragg wavelength of FBG 15 in response to physical distortion of fiber optic 14 due to change in relative pressure between primary fluid conduit 4 and secondary fluid conduit 5 at first flow region 21 and second flow region 23.

Further, the fluid disposed in primary fluid conduit 4 is introduced at port 6 bounded by wall 8 disposed in cover 40, flows through primary fluid conduit 4, is communicated through aperture 78 disposed in flexible membrane 22 and communicated to secondary fluid conduit 5, flows through secondary fluid conduit 5, is communicated through aperture 80 disposed in flexible membrane 22, is communicated through aperture 74 disposed in first flow member 2, and exits secondary fluid conduit 5 through port 11 bounded by wall 13 disposed in cover 40. It is contemplated that first flow region 21 overlaps second flow region 23 in a presence of FBG 15 of fiber optic 14. In this manner, secondary fluid conduit 5 is in fluid communication with primary fluid conduit 4 and receives the fluid from primary fluid conduit 4.

Figure 21:
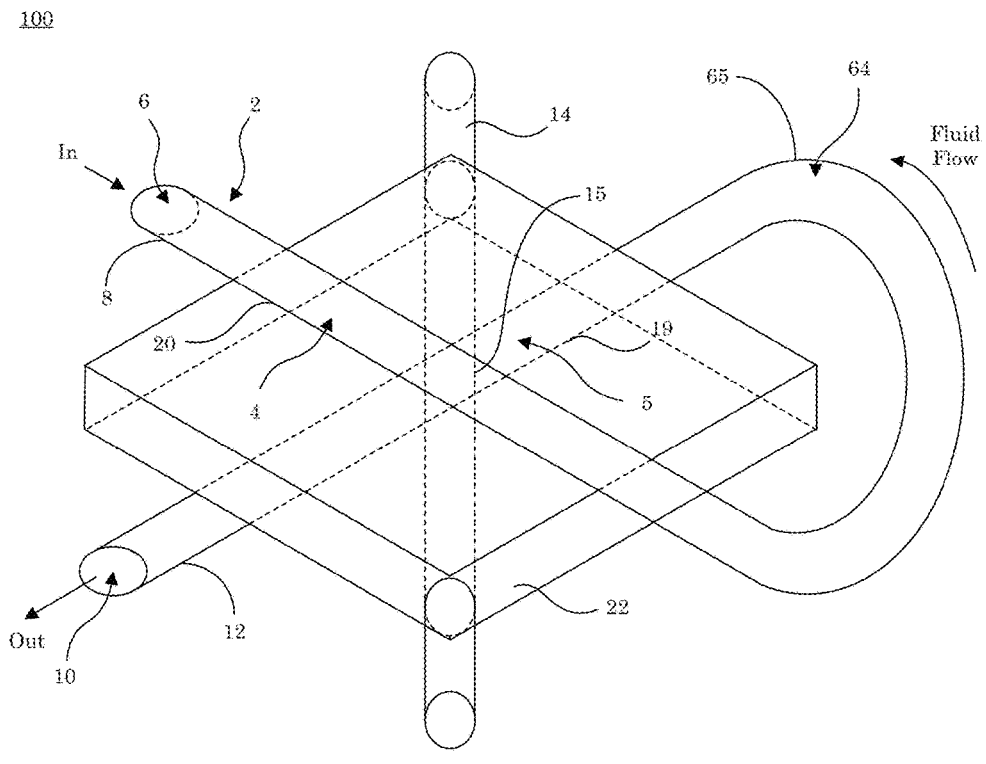
FIG. 21 shows an optofluidic flow meter.
Figure 21:
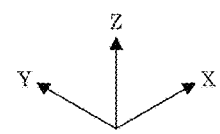
Figure 22:
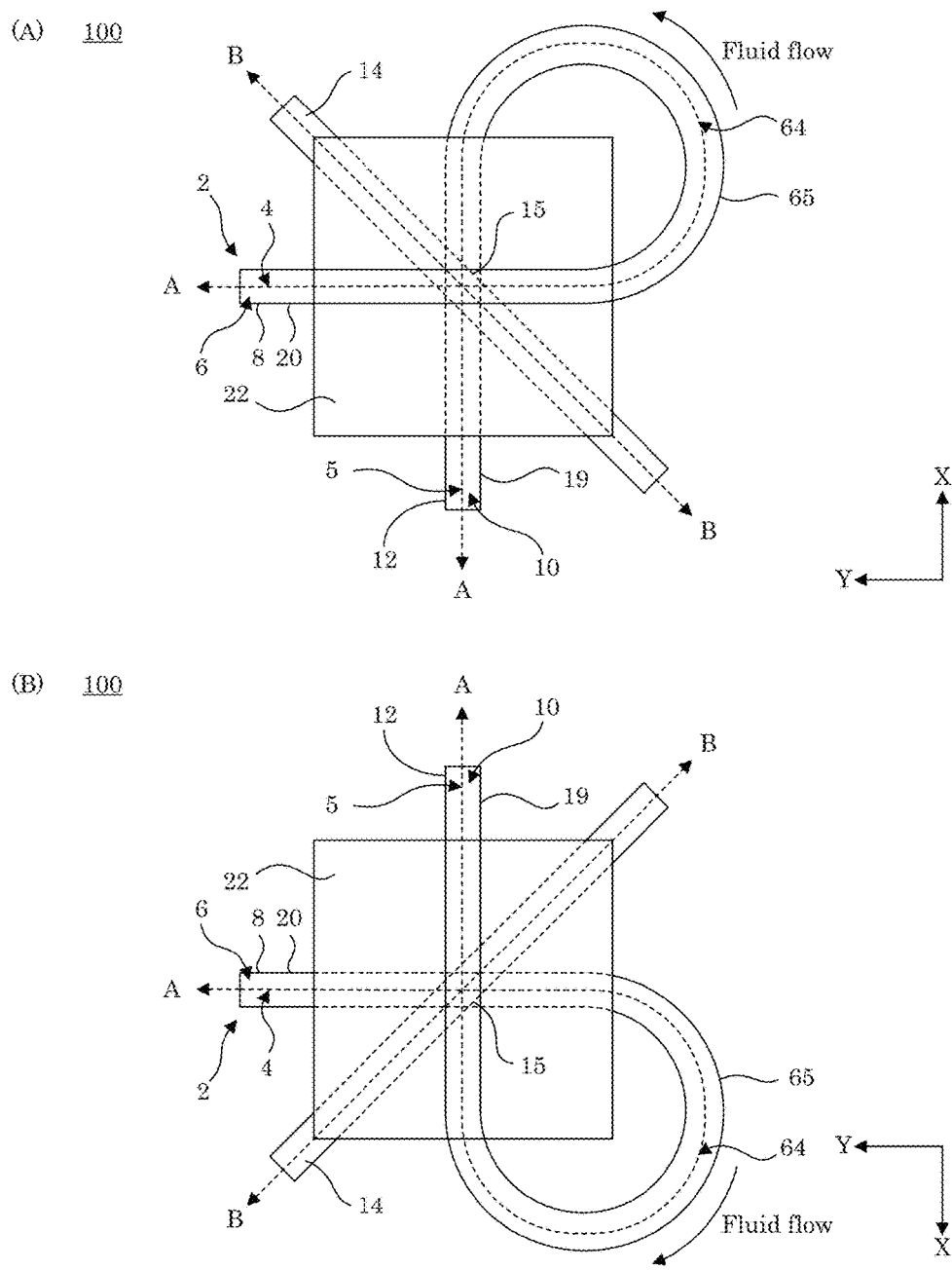
FIG. 22 shows a top view of the optofluidic flow meter shown in FIG. 21 in panel A, and panel B shows a bottom view.
Figure 23:
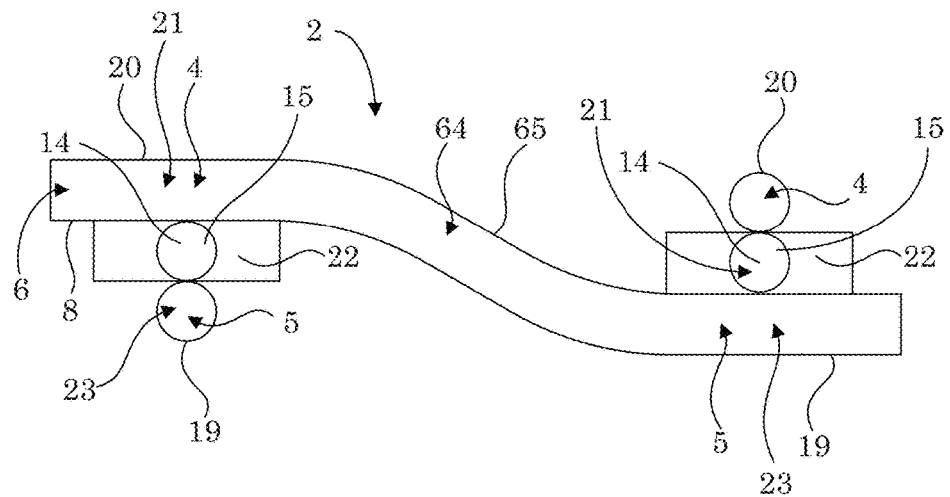
FIG. 23 shows a cross-section along line A-A of the optofluidic flow meter shown in FIG. 22 in panel A, and panel B shows a cross-section along line B-B.
Figure 23:
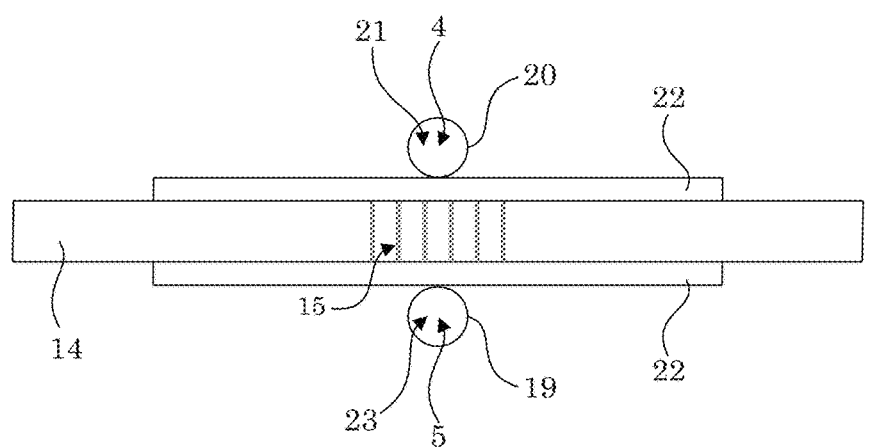

In an embodiment, with reference to FIG. 21, FIG. 22, and FIG. 23, optofluidic flow meter 100 includes flow member 2; primary fluid conduit 4 bounded by wall 20 and disposed in flow member 2 and that receives a fluid; secondary fluid conduit 5 bounded by wall 19 and disposed in second flow member 3 and that receives the fluid from primary fluid conduit 4; connector conduit 64 in fluid communication and fluidically interposed between primary fluid conduit 4 and secondary fluid conduit 5 and bounded by wall 65; and fiber optic 14 disposed in flexible membrane 22 and including fiber Bragg grating 15 interposed between first flow region 21 of primary fluid conduit 4 and second flow region 23 of secondary fluid conduit 5. Fiber optic 14 physically distorts relative to the pressure differential between primary fluid conduit 4 and secondary fluid conduit 5 and also produces the shift in Bragg wavelength in response to physical distortion of fiber optic 14 due to the pressure differential.

Here, fiber optic 14 physically distorts toward secondary fluid conduit 5 at second flow region 23 and away from primary fluid conduit 4 at first flow region 21 when a first pressure P1 of primary fluid conduit 4 is greater than a second pressure P2 of secondary fluid conduit 5, i.e., P1>P2. Also, fiber optic 14 physically distorts toward primary fluid conduit 4 at first flow region 21 of first flow member 2 and away from secondary fluid conduit 5 at second flow region 23 when first pressure P1 of primary fluid conduit 4 is less than second pressure P2 of secondary fluid conduit 5, i.e., P1<P2. When first pressure P1 of primary fluid conduit 4 is equal to second pressure P2 of secondary fluid conduit 5, i.e., P1=P2, fiber optic 14 is in a relaxed state instead of being physically distorted. In this manner, fiber optic 14 physically distorts relative to primary fluid conduit 4 and secondary fluid conduit 5 to respond to the pressure differential between primary fluid conduit 4 and secondary fluid conduit 5. Accordingly, fiber optic 14 produces the shift in Bragg wavelength of FBG 15 in response to physical distortion of fiber optic 14 due to change in relative pressure between primary fluid conduit 4 and secondary fluid conduit 5 at first flow region 21 and second flow region 23.

Further, the fluid disposed in primary fluid conduit 4 is introduced at port 6 bounded by wall 8 of flow member 2, flows through primary fluid conduit 4, flows through connector conduit 64 and communicated to secondary fluid conduit 5, flows through secondary fluid conduit 5, and exits secondary fluid conduit 5 through port 10 bounded by wall 12 of flow member 2. It is contemplated that first flow region 21 overlaps second flow region 23 in a presence of FBG 15 of fiber optic 14. In this manner, secondary fluid conduit 5 is in fluid communication with primary fluid conduit 4 and receives the fluid from primary fluid conduit 4.

In optofluidic flow meter 100, the flow member can include any material to support the fluid conduit. Exemplary materials for the flow member include soft polymeric materials such as elastomers (e.g. poly(dimethylsiloxane) (PDMS)), epoxies and adhesives (including tapes and photocurable adhesives), acrylics (e.g. polymethylmethacrylate (PMMA)), polycarbonates, polystyrenes, polyesters, polypropylenes, cyclic olefin copolymers and hard materials, such as glasses, semiconductor materials pure and doped silicon), and metals (e.g., aluminum). In an embodiment, the flow member includes PDMS. PMMA, organically modified ceramic technology, quartz, sapphire, and the like. The temperature of the flow member can be from −266° C. to 500° C., specifically from 0° C. to 100° C. and more specifically from 4° C. to 80° C.

Fluid flow through the fluid conduit in the flow member. The fluid can include a gas, liquid, or a combination thereof. Moreover, the first fluid disposed in primary fluid conduit 21 and the second fluid disposed in secondary fluid conduit 23 can be a same or different fluid. It is contemplated that the fluid can include solid particles disposed in a liquid or gas.

Exemplary fluids include water, bodily fluids, and organic solvents such as acetonitrile. The solid particles can include inorganic and organic micro- and nano-particles, biological materials such as proteins and protein aggregates, lipid vesicles, exosomes, organelles, and cells.

A pressure of the fluid in any of the fluid conduits can be from 1 Pa to 700 kPa, specifically from 1 Pa to 130 kPa, and more specifically from 1 Pa to 70 kPa. A pressure differential of the first fluid and second fluid can be from 1 Pa to 700 kPa, specifically from 1 Pa to 130 Pa, and more specifically from 1 Pa to 70 kPa. A viscosity of the fluid can be from $1\times10^{-6}$ to 1 Pa·s, specifically from $10\times10^{-6}$ to 0.1 Pa·s, and more specifically from $1\times10^{-4}$ to 0.01 Pa·s.

In optofluidic flow meter 100 the fiber-optic responds to a force exerted on the fiber-optic by physically distorting under such strain. The fiber optic includes the fiber Bragg grating disposed proximate to the flow region of the fluid conduit. Exemplary materials for the fiber optic include silica, organic polymers, and sapphire. The wavelength of reflected light by the fiber Bragg grating can be from 250 nm to 3000 nm, specifically from 250 nm to 3000 nm, and more specifically from 250 nm to 3000 nm. The shift in the Bragg wavelength of the reflected light can be from 0.0001 nm to 50 nm, specifically from 0.001 nm to 10 nm, and more specifically from 0.001 nm to 5 nm. In a particular embodiment, the wavelength of the reflected light is 1550 nm and the shift in the Bragg wavelength of the reflected light is from 0.00.1 nm to 0.5 nm at a force on the fiber Bragg grating of the fiber optic from 0.01 mN to 3 N.

The fiber-optic can be disposed in or on the flexible membrane. The flexible membrane can include any material to support the fiber optic and provide a selected flexibility with respect to pressure exerted on it by the fluid in the fluid conduit of the flow member. Exemplary materials for the flexible membrane include elastomers (e.g. PDMS), epoxies and adhesives (including tapes and photocurable adhesives), acrylics (e.g. PMMA), polycarbonates, polystyrenes, polyesters, polypropylenes, cyclic olefin copolymers. In an embodiment the flexible membrane includes PDMS made from Sylgard 184 (Dow Corning). It is contemplated that the flexible membrane communicates the force from the fluid conduit to the FBG within the fiber optic.

In the optofluidic flow meter, the cover can be disposed on the flow member. The cover can include any material to support flow in the flow member. Exemplary materials for the cover include polymeric materials such as epoxies and adhesives (including tapes and photocurable adhesives), acrylics (e.g. PMMA), polycarbonates, polystyrenes, polyesters, polypropylenes, cyclic olefin copolymers and hard materials, such as glasses, semiconductor materials (e.g. pure and doped silicon), and metals (e.g. aluminum). In an embodiment, the cover includes.

In the optofluidic flow meter, the substrate can be disposed on a flow member. The substrate can include any material to support flow in the flow member. Exemplary materials for the substrate include polymeric materials such as elastomers (e.g. PDMS), epoxies and adhesives (including tapes and photocurable adhesives), acrylics (e.g. PMMA), polycarbonates, polystyrenes, polyesters, polypropylenes, cyclic olefin copolymers and hard materials, such as glasses, semiconductor materials (e.g. pure and doped silicon), and metals (e.g. aluminum). In an embodiment, the substrate includes laser-cut PMMA.

In the optofluidic flow meter, the substrate can be disposed on a support. The support can include any material to support the substrate. Exemplary materials for the support include polymeric materials such as elastomers (e.g. PDMS), epoxies and adhesives (including tapes and photocurable adhesives), acrylics (e.g. PMMA), polycarbonates, polystyrenes, polyesters, polypropylenes, cyclic olefin copolymers and hard materials, such as glasses, semiconductor materials (e.g. pure and doped silicon), and metals (e.g. aluminum). In an embodiment, the support includes laser-cut PMMA.

In an embodiment, a process for making optofluidic flow meter 100 includes defining the flow channel in the support member. This process for defining the flow channel can involve subtractive (e.g. laser ablation, engraving, cutting, etching, etc.) or additive (e.g. 3D printing, controlled deposition, templated substrate growth, etc) manufacturing or photolithography to define topographic features. Additionally, the flow channel can be created by casting and curing a liquid material, such as uncured PDMS, epoxy, or adhesive, or embossing a solid material, such as acrylic, against a substrate having inverse topography of the desired flow channel features.

In an embodiment, a process for making optofluidic flow meter 100 includes incorporating an optical fiber having an FBG into a flexible membrane. Exemplary methods for incorporating the optical fiber include direct casting, exclusion molding, and cut outs.

Direct casting a membrane around an optical fiber involves pouring uncured membrane material over a fiber and allowing it to thin out before curing. In one embodiment, the thickness of the membrane was precisely controlled by attaching the optical fiber to a 4"-round silicon wafer. The membrane material was then poured over the fiber and the silicon wafer spun to remove excess membrane material. Spin speed can be altered to reliably control membrane thickness.

Exclusion molding involves creating topography features (such as utilizing one of the methods listed above) that will determine membrane thickness. In one embodiment, topographic features can be created on silicon wafers using photolithography. The negative photoresist SU8 was used as the photosensitive polymer to create the topographic patterns on a silicon wafer. In a preferred embodiment, the SU8 features were approximately the same height as the optical fiber diameter. The SU8 features included notched structures that precisely position the fiber in the membrane AND hold the fiber in place during exclusion. Other SU8 features, such as posts, are scattered around the surface to support the pressed substrate and maintain uniform height of the membrane. The SU8 features are typically treated with a silane to facilitate membrane removal after casting. The fiber is placed in the notches. In a preferred embodiment, a liquid material (e.g. PDMS, epoxy, optical adhesive) was poured over the surface to cover the posts. A glass slide (or similarly smooth, rigid material) is placed on top of the uncured membrane and pressed down to exclude the excess membrane material. In an alternative embodiment, a polymer melt can be pressed over the fiber and posts to embed the fiber in the polymer. The membrane is then cured (e.g. heat, ultraviolet light, time). The glass slide is removed and membrane (with fiber inside) can be pulled off the SU8 features.

In an embodiment, the fiber can be incorporated into a thin layer by cutting out a slot that the fiber can fit in. In one embodiment, a channel matching the fiber diameter was cut out of a piece of tape whose thickness matched the diameter of the optical fiber. If the tape was double sided, the tape further can be utilized to attach the membrane to the flow member and/or support. With the fiber in the membrane, the component layers of the Optical flow meter 100 can be assembled together. Exemplary methods for attaching components together include epoxies, tapes, cross-linking agents, oxygen plasma treatment, and clamping. Alignment of the FBG to the sensing region of the channel prior to attaching; the layers is ideally accomplished under magnification. In one embodiment, the layers were attached together by treating each with oxygen plasma and pressed together for covalent bonding. In another embodiment, the layers were from double sided tapes, which were stuck together after removing liners on the adhesives.

Figure 24:
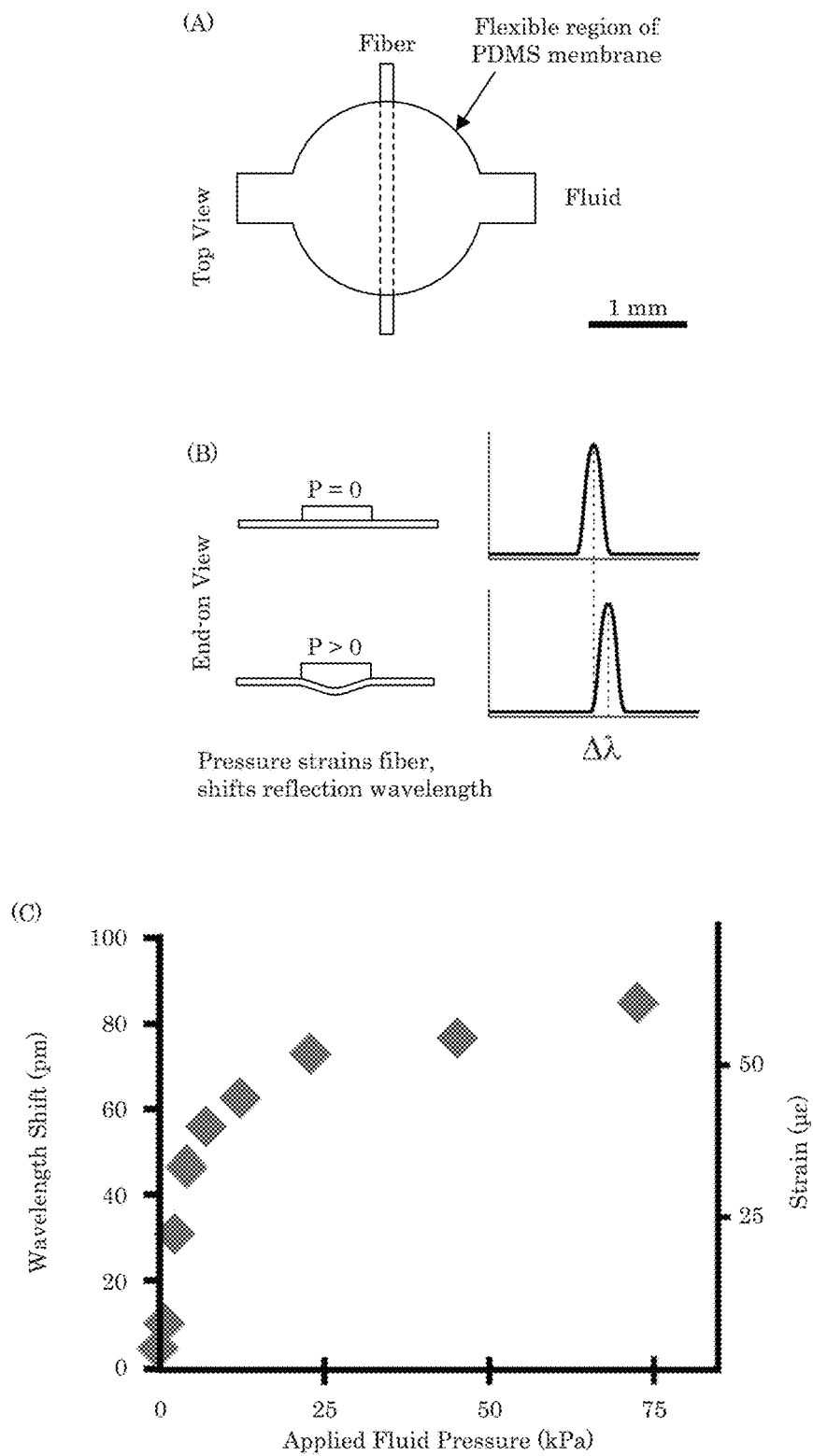
FIG. 24 shows a top view of an optofluidic flow meter; panel B shows physical distortion of a fiber optic and a shift of a Bragg wavelength of the fiber-optic in response to a pressure change in the flow member shown in panel A, and panel C shows a graph of wavelength shift versus applied fluid pressure.
Figure 25:
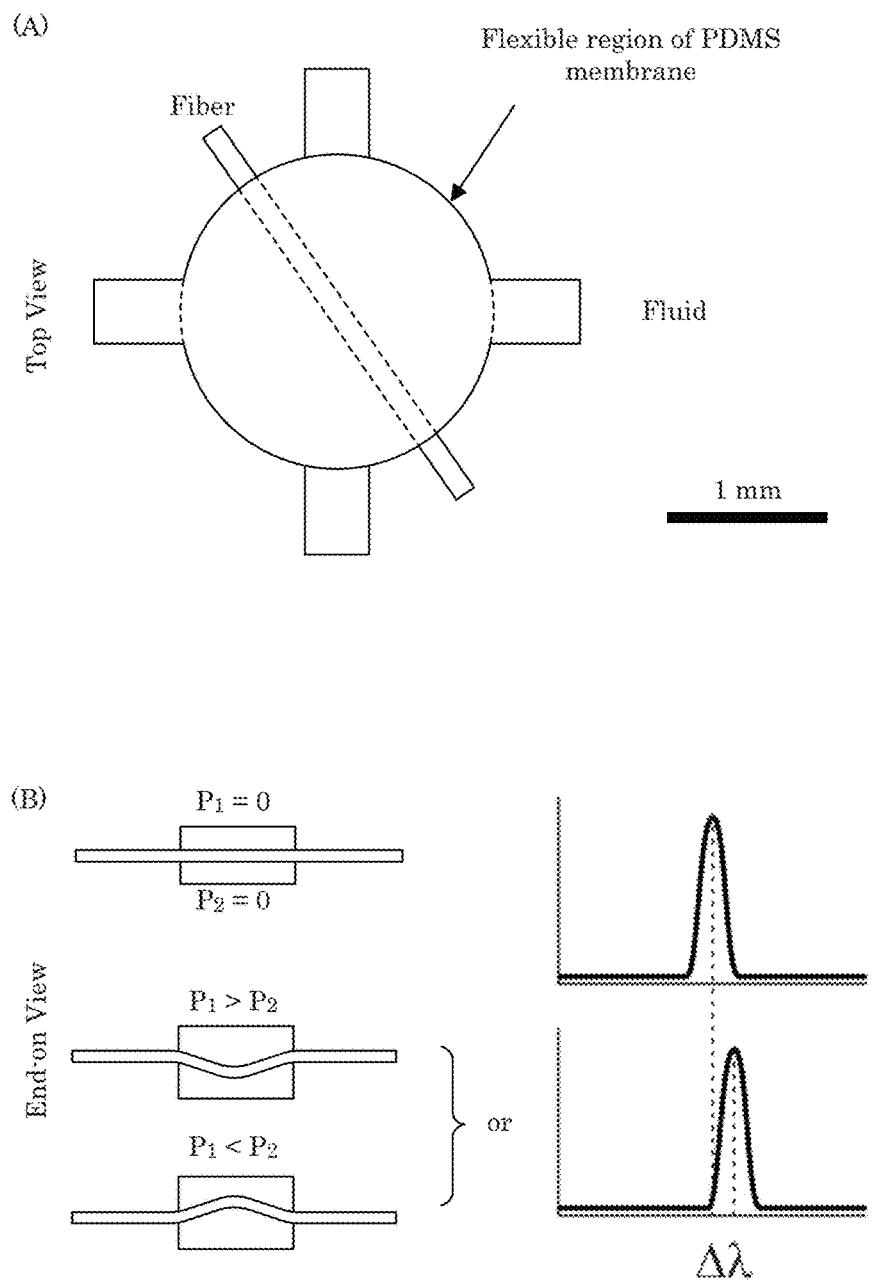
FIG. 25 shows a top view of an optofluidic flow meter, and panel B shows physical distortion of a fiber optic and a shift of a Bragg wavelength of the fiber-optic in response to a pressure change in the flow member shown in panel A.
Figure 26:
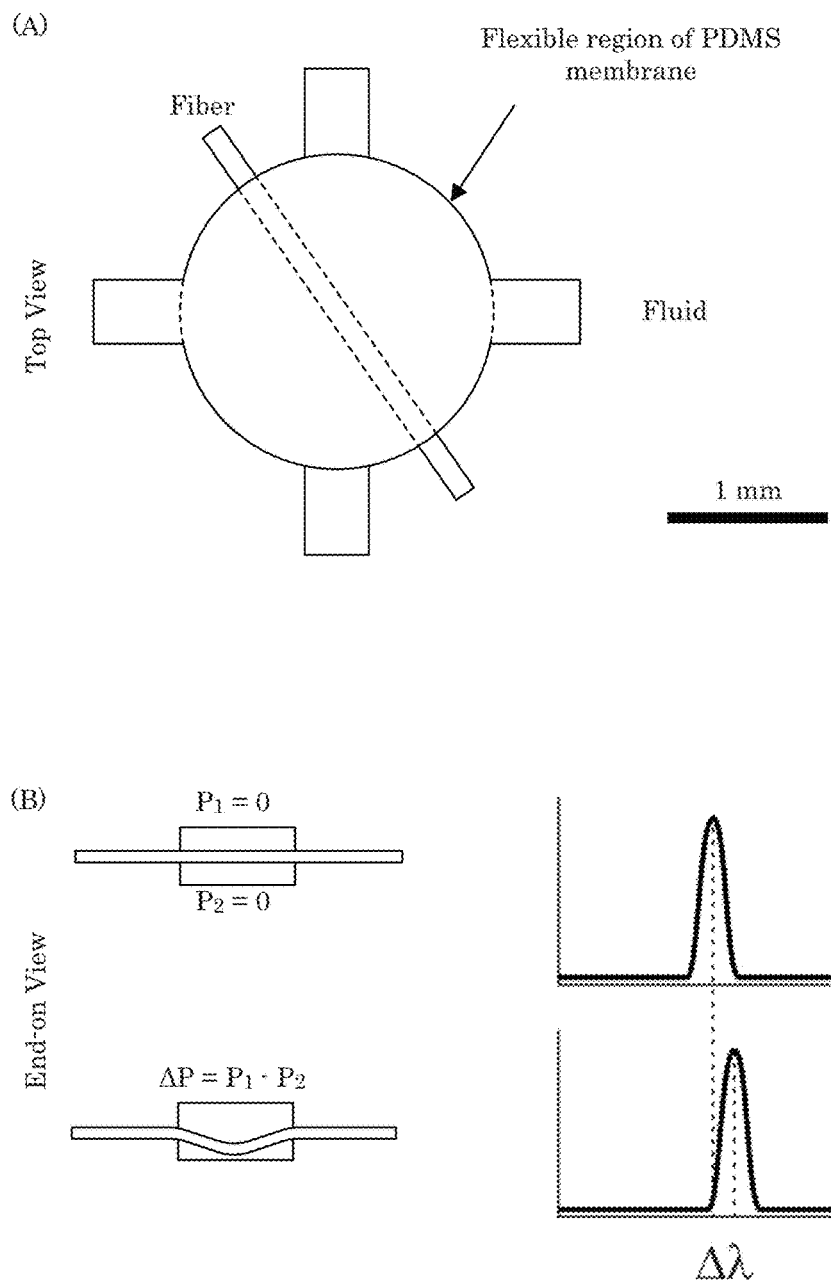
FIG. 26 shows a top view of an optofluidic flow meter, and panel B shows physical distortion of a fiber optic and a shift of a Bragg wavelength of the fiber-optic in response to a pressure change in the flow member shown in panel A.
Figure 27:
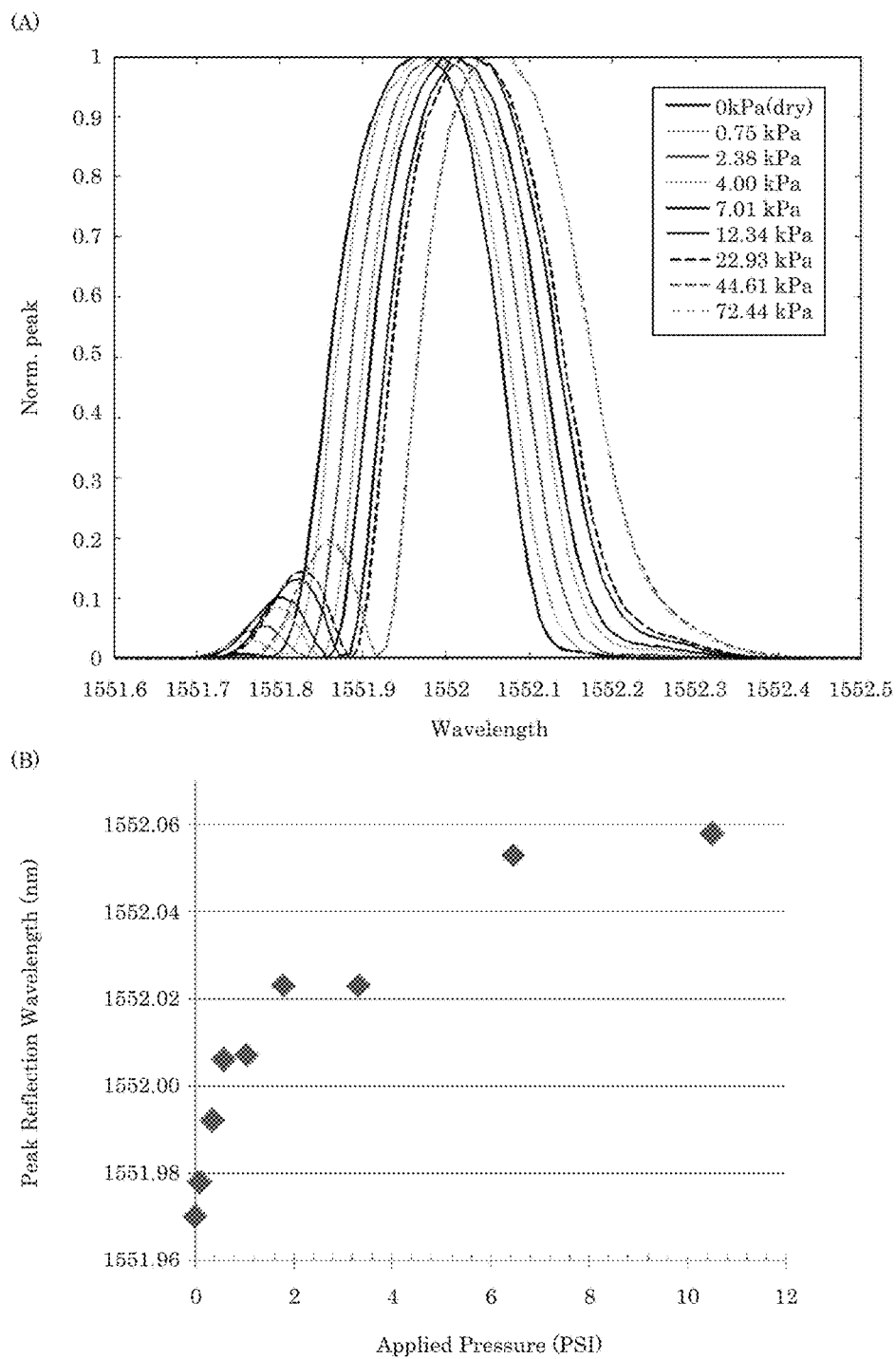
FIG. 27 shows a graph of reflected light intensity versus wavelength for varying fluid pressures against a Fiber Bragg Grating in panel A, and a graph of the waveglength at the peak reflected intensity versus applied pressure and panel B.
Figure 28:
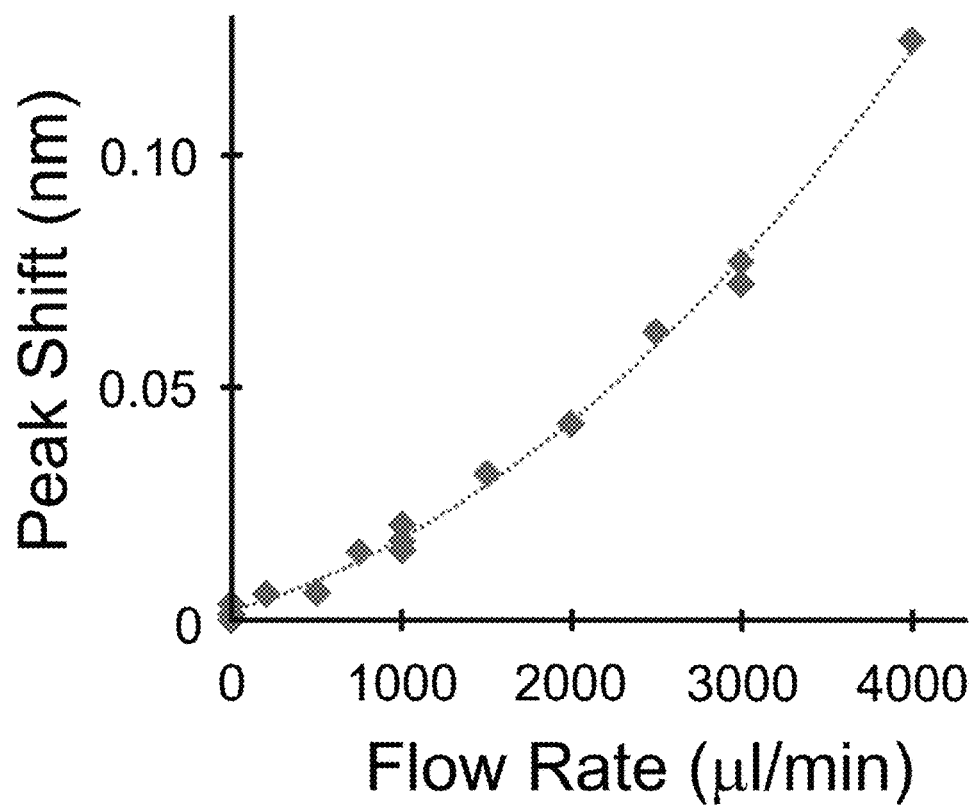
FIG. 28 shows a graph of peak shift versus flow rate for calibration of Bragg wavelength shift, as a function of flow rate roan optofluidic flow meter.

Optofluidic flow meter 100 has numerous beneficial uses, including determining a flow rate of a fluid in a fluid member. In an embodiment, a process for determining the flow rate of the fluid in the fluid member includes attaching the optical fiber via a to a light source and a wavemeter and monitoring either the peak wavelength of the light reflected from the FBG or the peak absorption of the light transmitted through the FBG at the exit of the fiber optic. In one embodiment, as shown in FIG. 24 through 27, we monitored the reflected signal as fluids were passed through the device. In one embodiment, fluid pressures were modified using a pressure controller over a column of water and the FBG wavelength shift was monitored as shown in FIG. 24 and FIG. 27. In another embodiment, a defined flow rate was injected (via syringe pump) into the Optofluidic flow meter 100 to calibrate the Bragg wavelength shift as a function of flow, as shown in FIG. 28. Unknown flows can then be determined by extrapolating along a fit to this data.

Optofluidic flow meter 100 has numerous advantageous and beneficial properties. In an aspect, the device enables in situ measurement of pressure without altering the fluid flow.

Advantageously, unexpectedly, and surprisingly, optofluidic flow meter 100 provides the ability to compare fluid pressures of two fluids impinging on a single FBG and enables the precise calibration of fluid flow according to the pressure drop through a flow channel that passes from one side of the membrane-embedded FBG to the other side of the FBG.

The optofluidic flow meter shifts the Bragg wavelength of reflected light linearly from 3 to 4 orders of magnitude of pressure change.

The articles and processes herein are illustrated further by the following Examples, which are non-limiting.

EXAMPLES

Example 1

Optofluidic Flow Meter with Dual Fiber Optics

An optofluidic flow meter shown in FIG. 11-FIG. 15 was constructed as follows. Here, a fiber optic with an FBG was disposed on a flexible membrane that was interposed between a microfluidic channel as a fluid conduit and above a receptacle that was round and into which the flexible membrane and optical fiber was displaced during physical distortion. A 180-µm thick PDMS flexible membrane was fabricated, disposed over a 125-µm diameter FBG, and aligned across the receptacle that was a 2-mm diameter deformation region located below the microfluidic channel. Layers were bonded using either double sided tapes that were cut or subjected to oxygen plasma activation to provide the fluid conduit. Pressure of the fluid that flowed through the fluid conduit was controlled by a column of water subject to the force of gravity or, for higher pressures, was controlled by air pressure above a column of water. The optofluidic flow meter responded to pressure changes in the fluid flowing through the fluid conduit, which strained the optical fiber in the flexible membrane as shown in FIG. 24. With regard to FIG. 24, panel A shows a top view of the flow region and flexible membrane with the FBG which reflected wavelength exhibit shifts in Bragg wavelength due to pressure of the fluid in the fluid conduit. Further data is shown in FIG. 27. Sensitivity of the shift in Bragg wavelength due to the pressure of the fluid was on the order of 0.1 psi (700 Pa, 4 mN) on the flexible membrane.

Example 2

Optofluidic Flow Meter with Single Fiber Optic

An optofluidic flow meter shown in FIG. 16-FIG. 20 was constructed as follows. Exclusion molding was used to dispose a fiber optic with a fiber Bragg grating in a flexible member. Here, features that determined a height of the flexible membrane were patterned on surface a silicon wafers using photolithography. We demonstrated this capability by creating SU8 (a type of photoresist) features that were the same height as the optical fiber (125 micrometers). The SU8 features included posts that positioned the fiber in the membrane and held hold the fiber in place during membrane exclusion. The SU8 features (e.g., posts) were selectively disposed on the surface to support the exclusion substrate and maintained uniform height across the wafer. The SU8 features were treated with a silane to facilitate membrane removal. The optical fiber was disposed among the notches, and material for the flexible membrane (e.g. PDMS, epoxy, optical adhesive) was poured over the surface. A smooth rigid member such as a glass slide was disposed on top of the uncured flexible membrane and pressed to exclude excess material from the flexible membrane. The flexible membrane was cured by, e.g. heat, ultraviolet light, time, and the like. The glass slide was removed, and the flexible membrane that included the optical fiber were removed from the SU8 features. The flexible membrane was disposed in a microfluidic system that included a flow member and fluid conduit. The flexible membrane can be attached to the flow member using, e.g., adhesive (e.g., tape), chemical crosslinking, oxygen plasma activation, heat, and the like. FIG. 26 shows a top view of the fabricated optofluidic flow meter in panel A and a response to a pressure differential of a shift in the Bragg wavelength of reflected light in panel B.

Example 3

Optofluidic Flow Meter System

Figure 16:
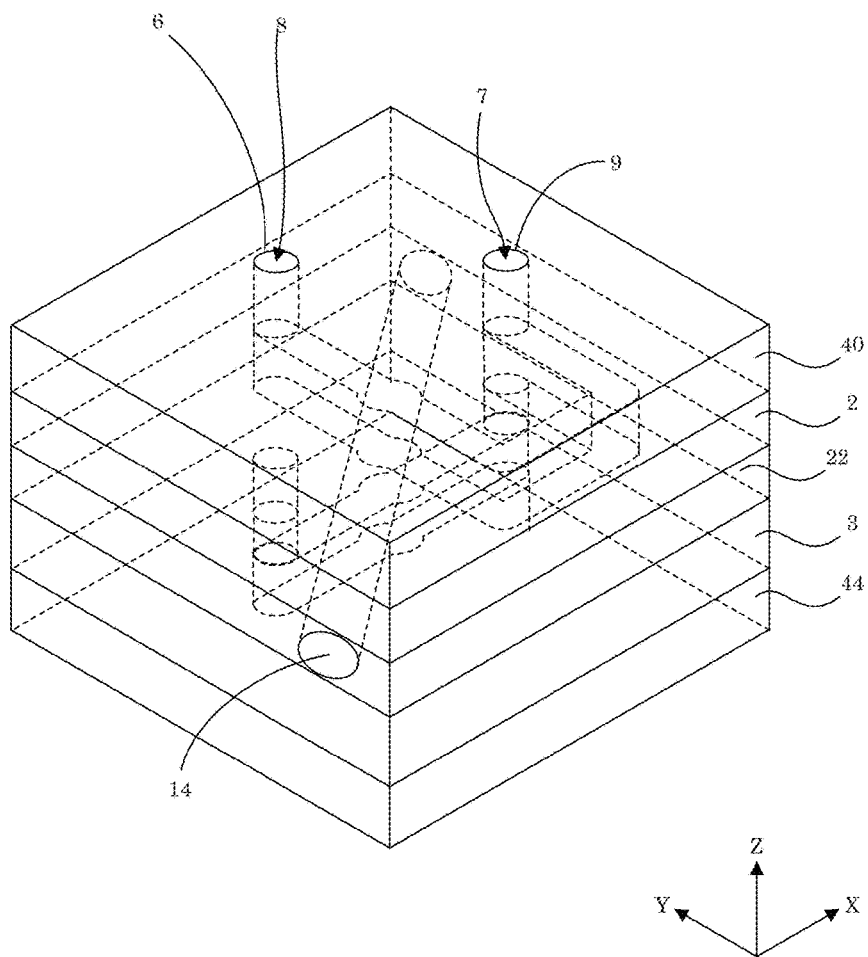
FIG. 16 shows an optofluidic flow meter.
Figure 17:
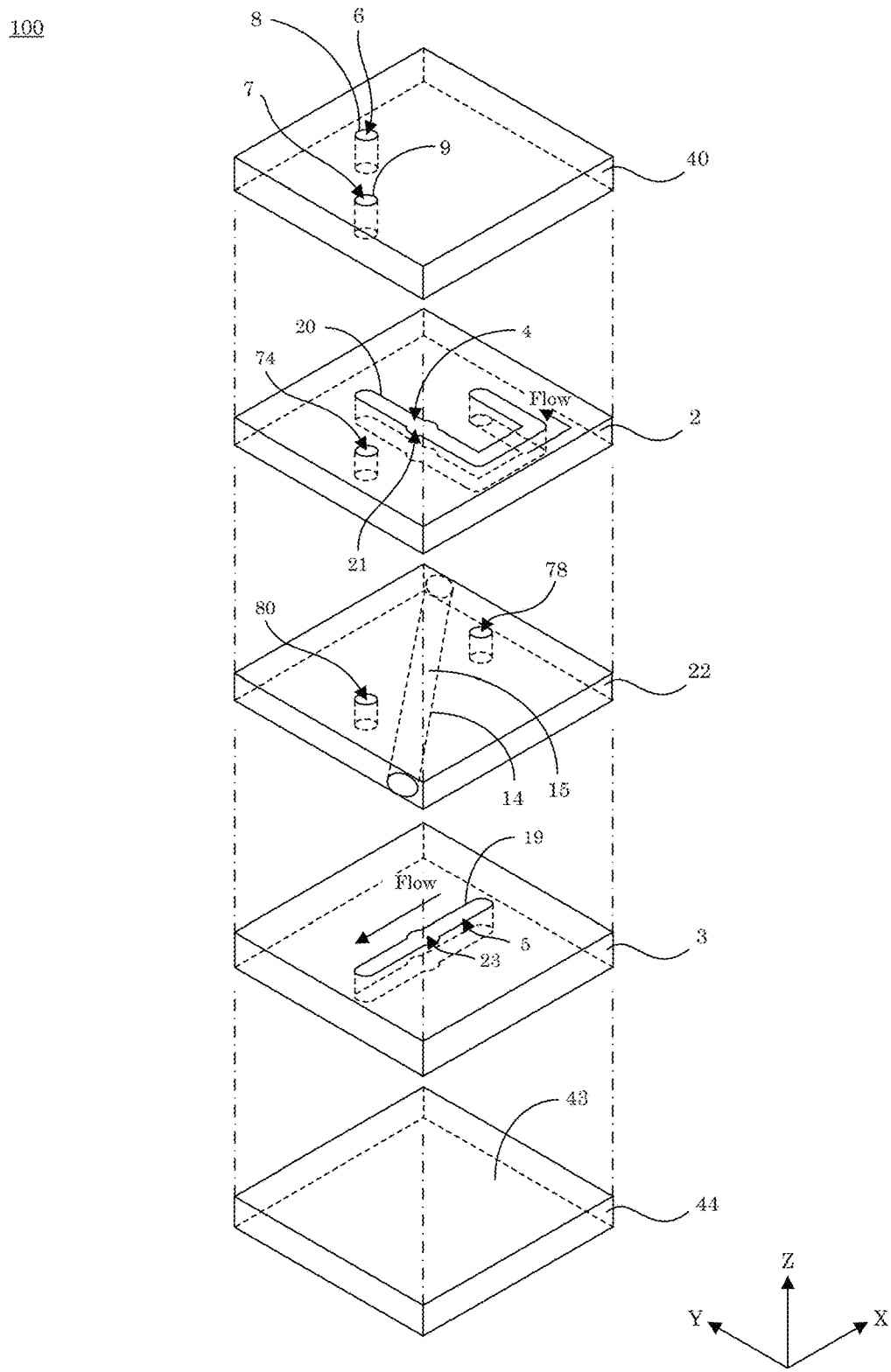
FIG. 17 shows an exploded view of the optofluidic flow meter shown in FIG. 16.
Figure 18:
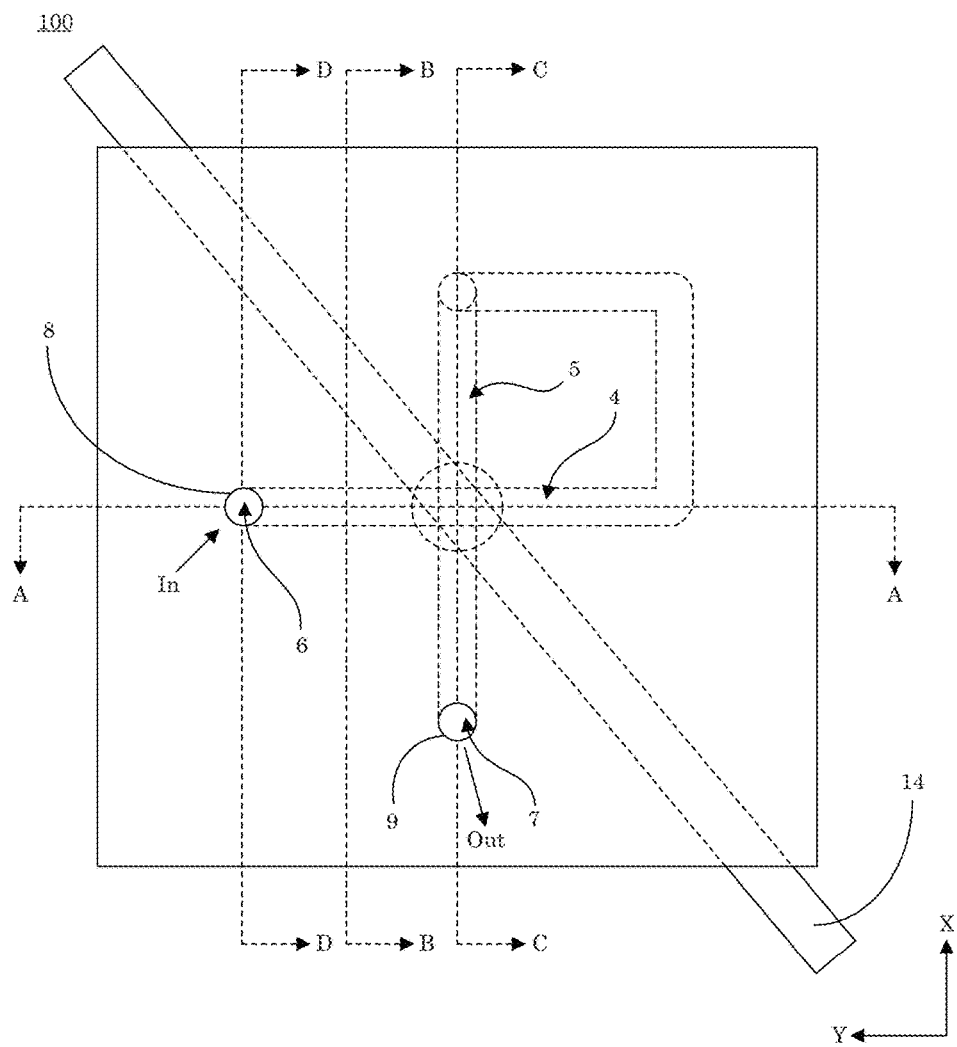
FIG. 18 shows a top view of the optofluidic flow meter shown in FIG. 16.
Figure 19:
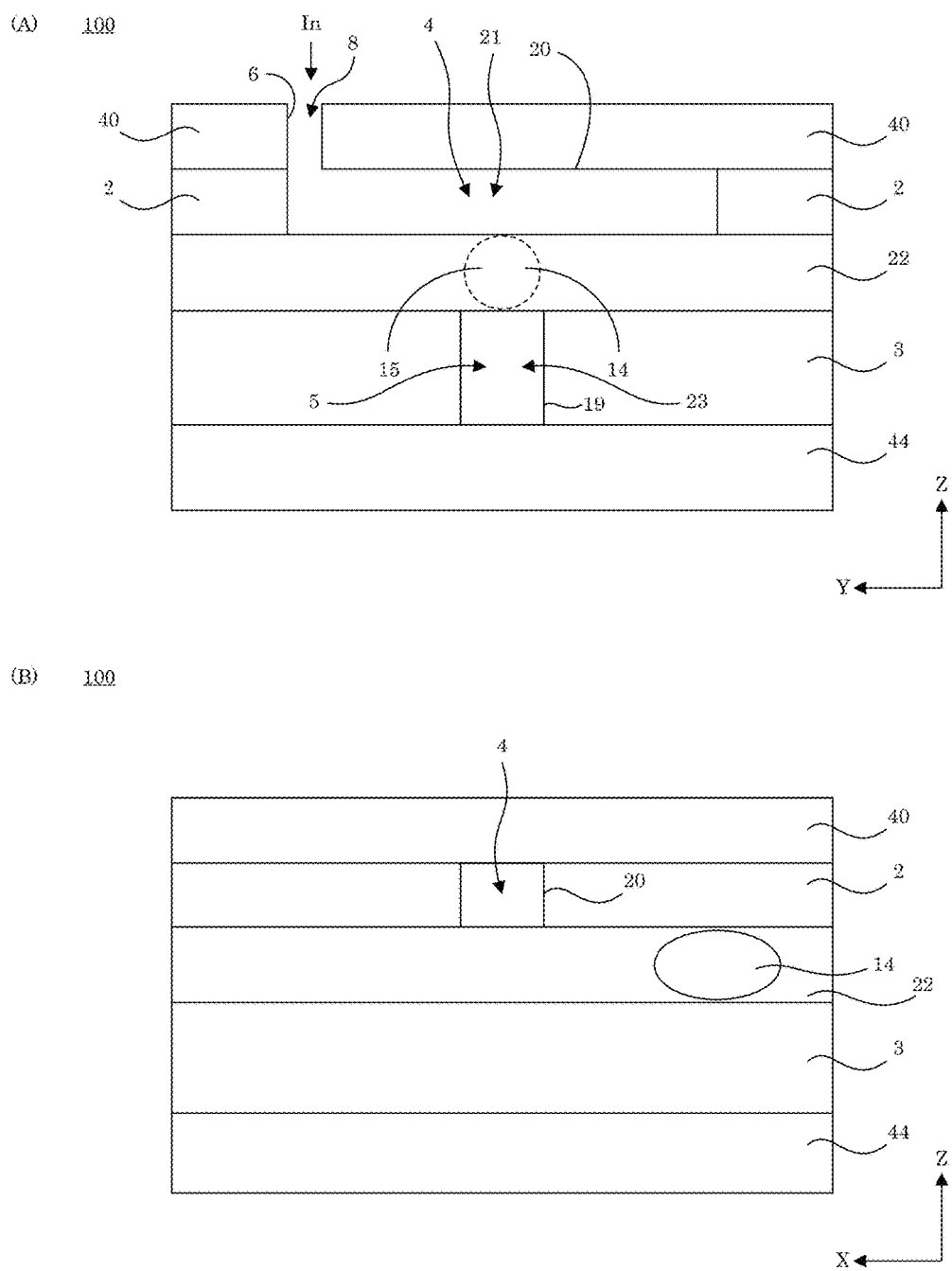
FIG. 19 shows a cross-section along line A-A of the optofluidic flow meter shown in FIG. 18 in panel A, and panel B shows a cross-section along line B-B.
Figure 20:
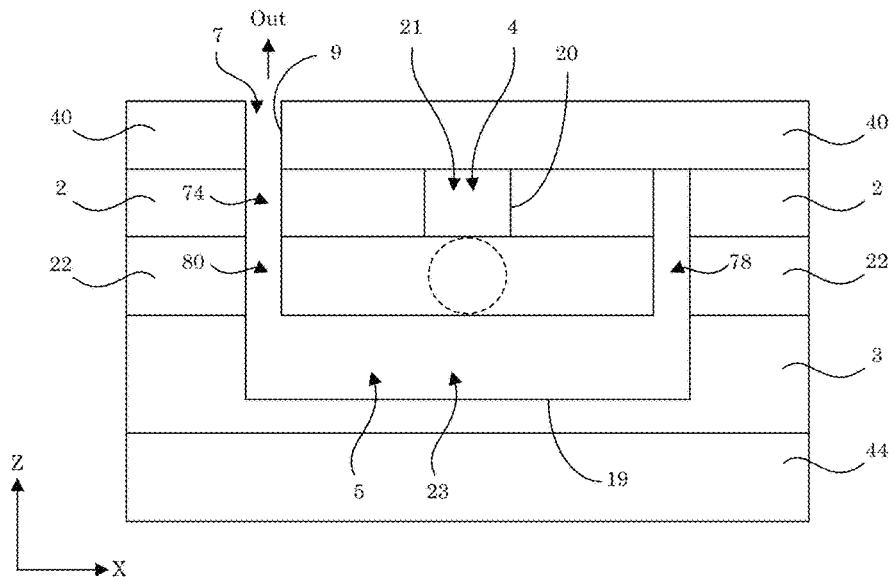
FIG. 20 shows a cross-section along line C-C of the optofluidic flow meter shown in FIG. 18 in panel A, and panel B shows a cross-section along line D-D.
Figure 20:
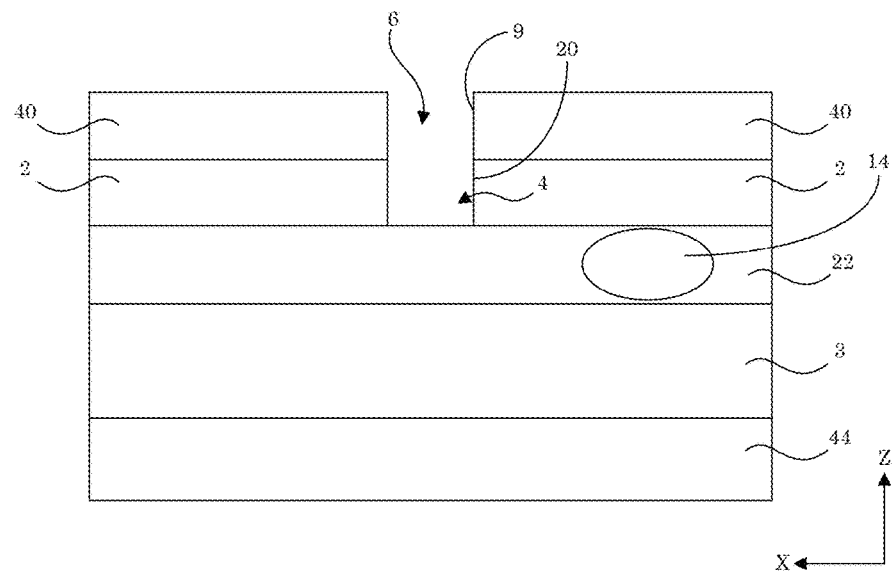

An optofluidic flow meter system is shown in FIG. 16 and FIG. 26, and results from of the optofluidic flow meter system are shown in FIG. 28. Here, poly(dimethylsiloxane) (PDMS) flexible membranes were acquired from a commercial source or cured from spun-coat PDMS. Laser-cut double-sided silicone tape was used to adhere layers together and to form microfluidic channels as fluid conduits. Commercially available FBG with Bragg resonance wavelengths from 1540 nm to 1560 nm were adhered to fluid conduits into the PDMS flexible membranes of approximately the same thickness as the fiber diameter. Peak resonance of FBG-s was determined after scanning a laser over the resonance region and measuring the power of the reflected signal. Fluid temperatures were controlled using a temperature controlled water bath. Liquid pressure was controlled using a column of water and a pressure regulator over the water.

The fluid conduit in the flow member provided contact of less than 1 ml of fluid above the FBG of the flow meter. Shifts in the Bragg wavelength were calibrated for flows ranging from 50 to 6000 µl/min.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An optofluidic flow meter to determine a rate of fluid flow in a flow member, the optofluidic flow meter comprising:
   the flow member;
   a primary fluid conduit disposed in the flow member and that receives a fluid;
   a secondary fluid conduit disposed in the flow member; and
   a fiber optic comprising a fiber Bragg grating interposed between a first flow region of the primary fluid conduit and a second flow region of the secondary fluid conduit and that:
      physically distorts relative to a pressure differential between the primary fluid conduit and the secondary fluid conduit; and
      produces a shift in a Bragg wavelength in response to a physical distortion due to the pressure differential.

2. The optofluidic flow meter of claim 1, wherein the secondary fluid conduit is in fluid communication with the primary fluid conduit and receives the fluid from the primary fluid conduit.

3. The optofluidic flow meter of claim 1, wherein the secondary fluid conduit is isolated from fluid communication with the primary fluid conduit and receives a second fluid.

4. The optofluidic flow meter of claim 1, further comprising a flexible membrane interposed between the first flow region and the second flow region and that physically distorts relative to the pressure differential between the primary fluid conduit and the secondary fluid conduit.

5. The optofluidic flow meter of claim 4, wherein the fiber Bragg grating is disposed in the flexible membrane.

6. The optofluidic flow meter of claim 4, wherein the fiber Bragg grating comprises a silica, an organic polymer, a sapphire, or a combination comprising at least one of the foregoing materials.

7. The optofluidic flow meter of claim 1, wherein the flow member comprises an elastomer, an acrylic, an adhesive, or a combination comprising at least one of the foregoing materials.

8. The optofluidic flow meter of claim 1, wherein the primary fluid conduit comprises a cross-sectional area orthogonal to a direction of the fluid flow at the first flow region from 1 micrometers squared to 1000000 micrometers squared.

9. The optofluidic flow meter of claim 1, wherein the secondary fluid conduit comprises a cross-sectional area orthogonal to a direction of the fluid flow at the second flow region from 1 micrometers squared to 1000000 micrometers squared.

10. The optofluidic flow meter of claim 1, wherein the pressure differential is from 50 milliNewton to 3 Newtons.

11. The optofluidic flow meter of claim 10, wherein the shift in the Bragg wavelength is from 0.001 nanometers to 0.5 nanometers.

12. The optofluidic flow meter of claim 1, wherein the fluid comprises a liquid.

13. The optofluidic flow meter of claim 12, wherein the fluid further comprises a plurality of solid particles disposed in the liquid.

14. The optofluidic flow meter of claim 13, wherein the shift in the Bragg wavelength is in response to a presence of the solid particles.

* * * * *